(12) United States Patent
Ishizaki et al.

(10) Patent No.: US 10,314,957 B2
(45) Date of Patent: Jun. 11, 2019

(54) BLOOD PURIFICATION APPARATUS

(71) Applicant: Nikkiso Company Limited, Tokyo (JP)

(72) Inventors: Fumihiko Ishizaki, Shizuoka (JP); Satoshi Takeuchi, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 187 days.

(21) Appl. No.: 15/387,913

(22) Filed: Dec. 22, 2016

(65) Prior Publication Data

US 2017/0095602 A1    Apr. 6, 2017

Related U.S. Application Data

(63) Continuation of application No. PCT/JP2015/068562, filed on Jun. 26, 2015.

(30) Foreign Application Priority Data

Jun. 27, 2014  (JP) ................................. 2014-133035

(51) Int. Cl.
*A61N 1/14* (2006.01)
*A61M 1/16* (2006.01)
(Continued)

(52) U.S. Cl.
CPC ............ *A61M 1/1605* (2014.02); *A61M 1/14* (2013.01); *A61M 1/16* (2013.01); *A61M 1/1694* (2013.01);
(Continued)

(58) Field of Classification Search
None
See application file for complete search history.

(56) References Cited

U.S. PATENT DOCUMENTS 9,192,708 B2   11/2015  Iwahori et al.
2012/0128533 A1*  5/2012  Deguchi ................. F04B 13/00
                                                                422/62
(Continued)

FOREIGN PATENT DOCUMENTS

JP    H03073162 A    3/1991
JP    2003093501 A   4/2003
(Continued)

OTHER PUBLICATIONS

International Search Report from the Japanese Patent Office for Application No. PCT/JP2015/068562, dated Oct. 6, 2015.
(Continued)

*Primary Examiner* — Chester T Barry
(74) *Attorney, Agent, or Firm* — The Dobrusin Law Firm, PC

(57) ABSTRACT

A blood purification apparatus is provided that can easily and accurately determine before treatment whether or not blocking of liquid by a check valve is appropriate. In the blood purification apparatus including a blood circuit, a dialyzer, a dialysate introduction line and a dialysate discharge line, pressure detection device, a dialysate extraction device, a dialysate supply line, and a check valve that blocks flow of a liquid from the blood circuit to the dialysate introduction line, there are provided a control means that makes it possible to generate a pressure difference between a side of the blood circuit and a side of the dialysate introduction line across the check valve, a monitor means that makes it possible to monitor a change in a detection value of the pressure detection device based on the pressure difference, and a determination means that makes it possible to determine whether or not blocking of liquid by the check valve is appropriate based on the change in the detection value of the pressure detection device.

14 Claims, 17 Drawing Sheets

(51) Int. Cl.

| | | |
|---|---|---|
| *A61M 1/14* | (2006.01) | |
| *A61M 1/26* | (2006.01) | |
| *A61M 1/36* | (2006.01) | |
| *A61M 39/24* | (2006.01) | |
| *B01D 61/14* | (2006.01) | |
| *B01D 61/22* | (2006.01) | |
| *A61M 1/34* | (2006.01) | |

(52) U.S. Cl.
CPC .......... *A61M 1/267* (2014.02); *A61M 1/3465* (2014.02); *A61M 1/3638* (2014.02); *A61M 1/3653* (2013.01); *A61M 1/3656* (2014.02); *A61M 39/24* (2013.01); *B01D 61/145* (2013.01); *B01D 61/22* (2013.01); *A61M 2205/15* (2013.01); *A61M 2205/3331* (2013.01)

(56) References Cited

U.S. PATENT DOCUMENTS

| | | |
|---|---|---|
| 2013/0292313 A1 | 11/2013 | Fava et al. |
| 2014/0138301 A1 | 5/2014 | Iwahori et al. |
| 2014/0345574 A1* | 11/2014 | Haefele .............. F02M 25/0809 123/519 |
| 2015/0198081 A1* | 7/2015 | Surnilla .............. F02D 41/3094 123/294 |
| 2017/0261124 A1* | 9/2017 | Delgado .............. F16K 37/0083 |

FOREIGN PATENT DOCUMENTS

| | | |
|---|---|---|
| JP | 2004313522 A | 11/2004 |
| JP | 2009207706 A | 9/2009 |
| JP | 2010184029 A | 8/2010 |
| JP | 2011161060 A | 8/2011 |
| JP | 2013027494 A | 2/2013 |
| JP | 2013027495 A | 2/2013 |
| WO | 2009/074588 A1 | 6/2009 |
| WO | 2013/151114 A1 | 10/2013 |

OTHER PUBLICATIONS

Written Opinion from the Japanese Patent Office for Application No. PCT/JP2015/068562, dated Oct. 6, 2015.
Co-pending U.S. Appl. No. 14/163,051, filed Jan. 24, 2014, published as US 2014/0138301.
Co-pending U.S. Appl. No. 14/197,329, filed Mar. 5, 2014, granted as U.S. Pat. No. 9,192,708.
Co-pending U.S. Appl. No. 15/384,993, filed Dec. 20, 2016.

\* cited by examiner

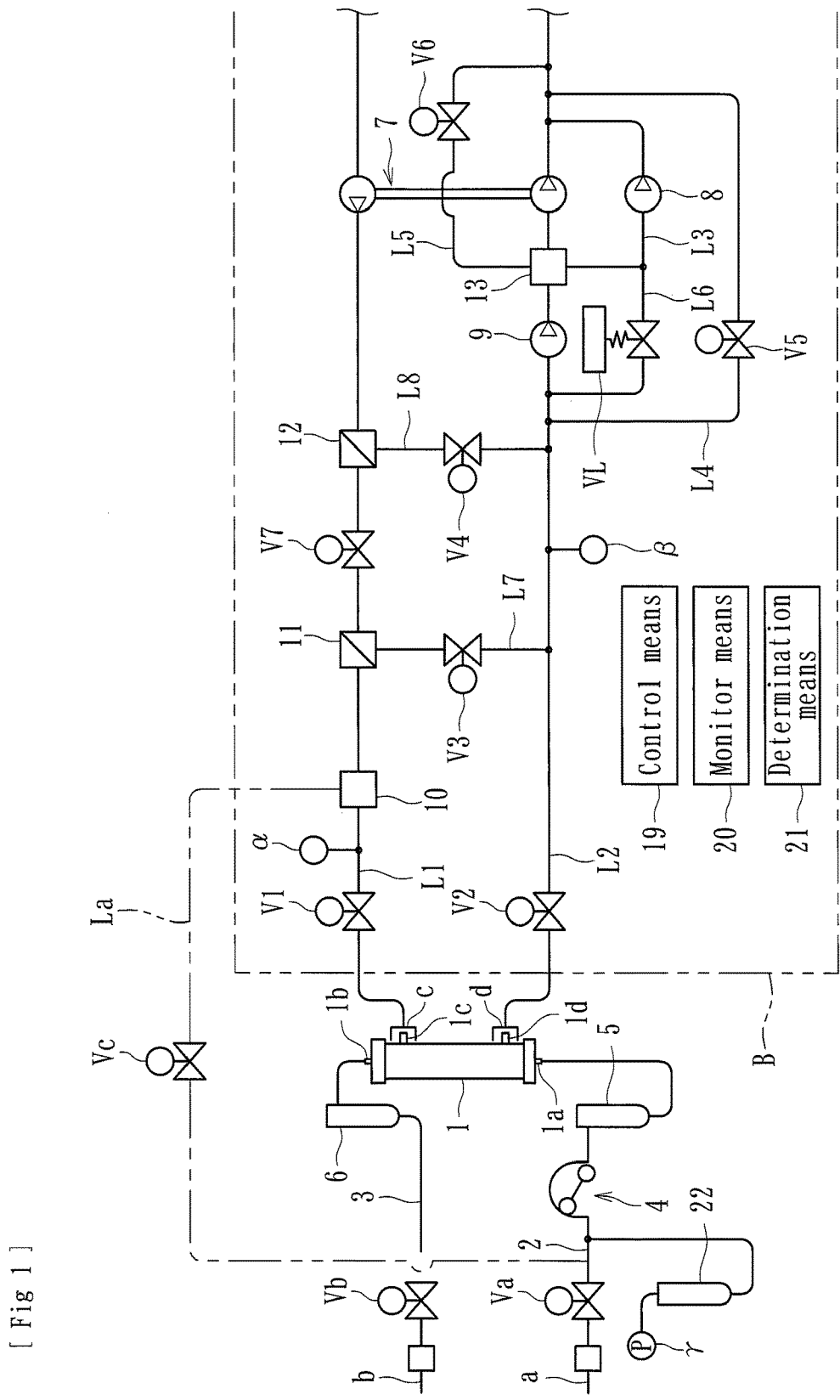
[Fig 1]

[Fig 2]
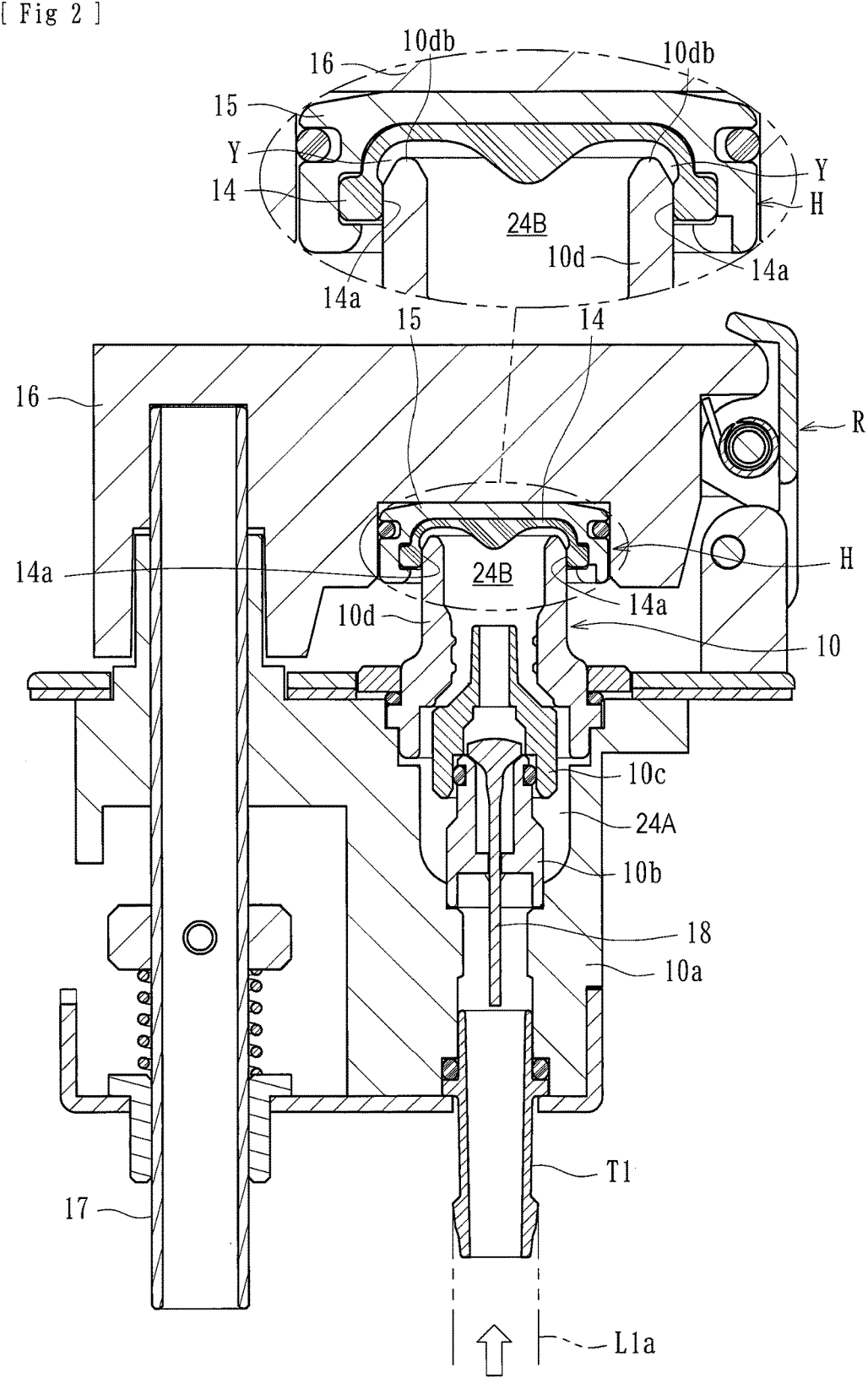

[Fig 3]
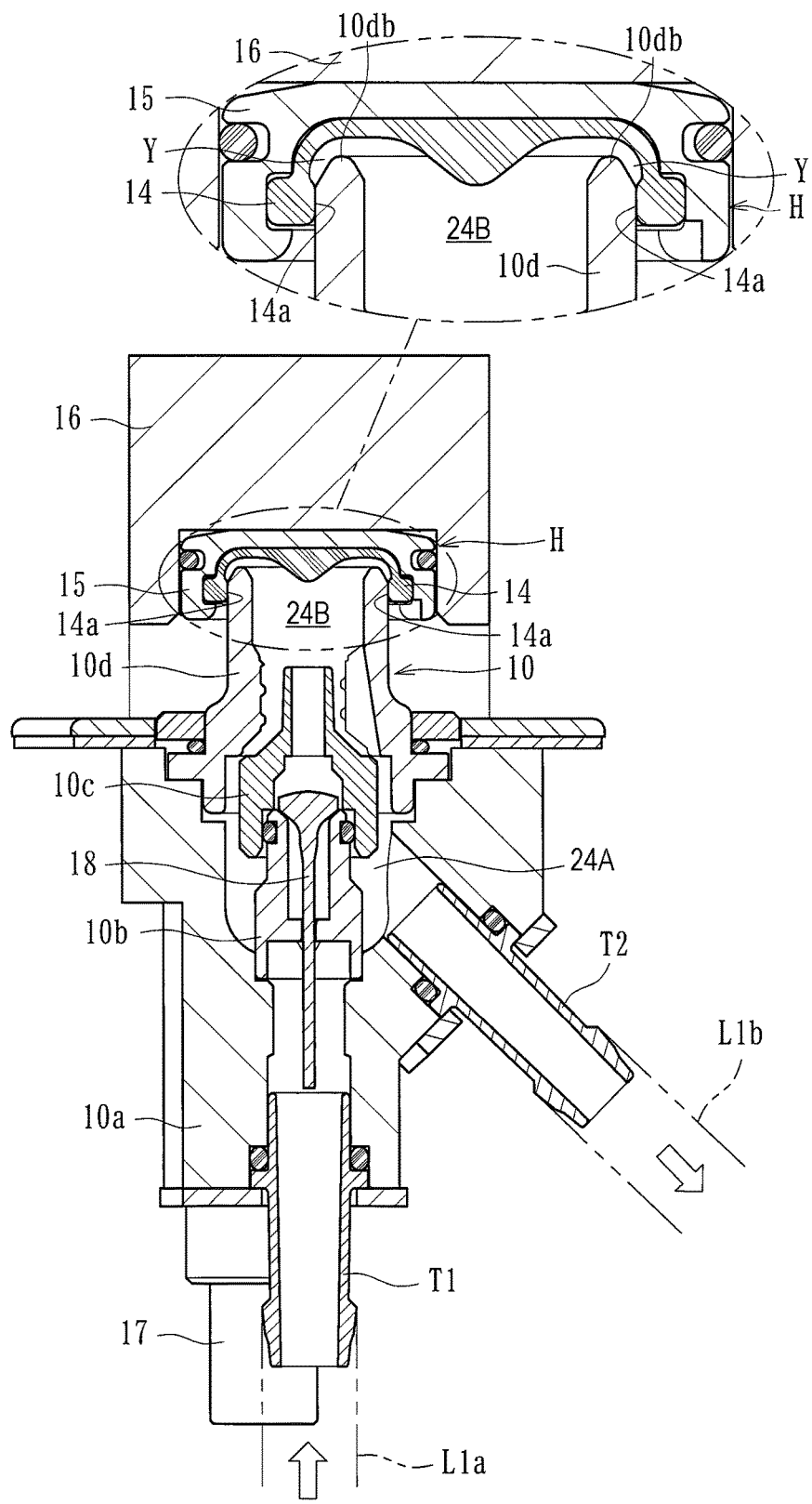

[Fig 4]
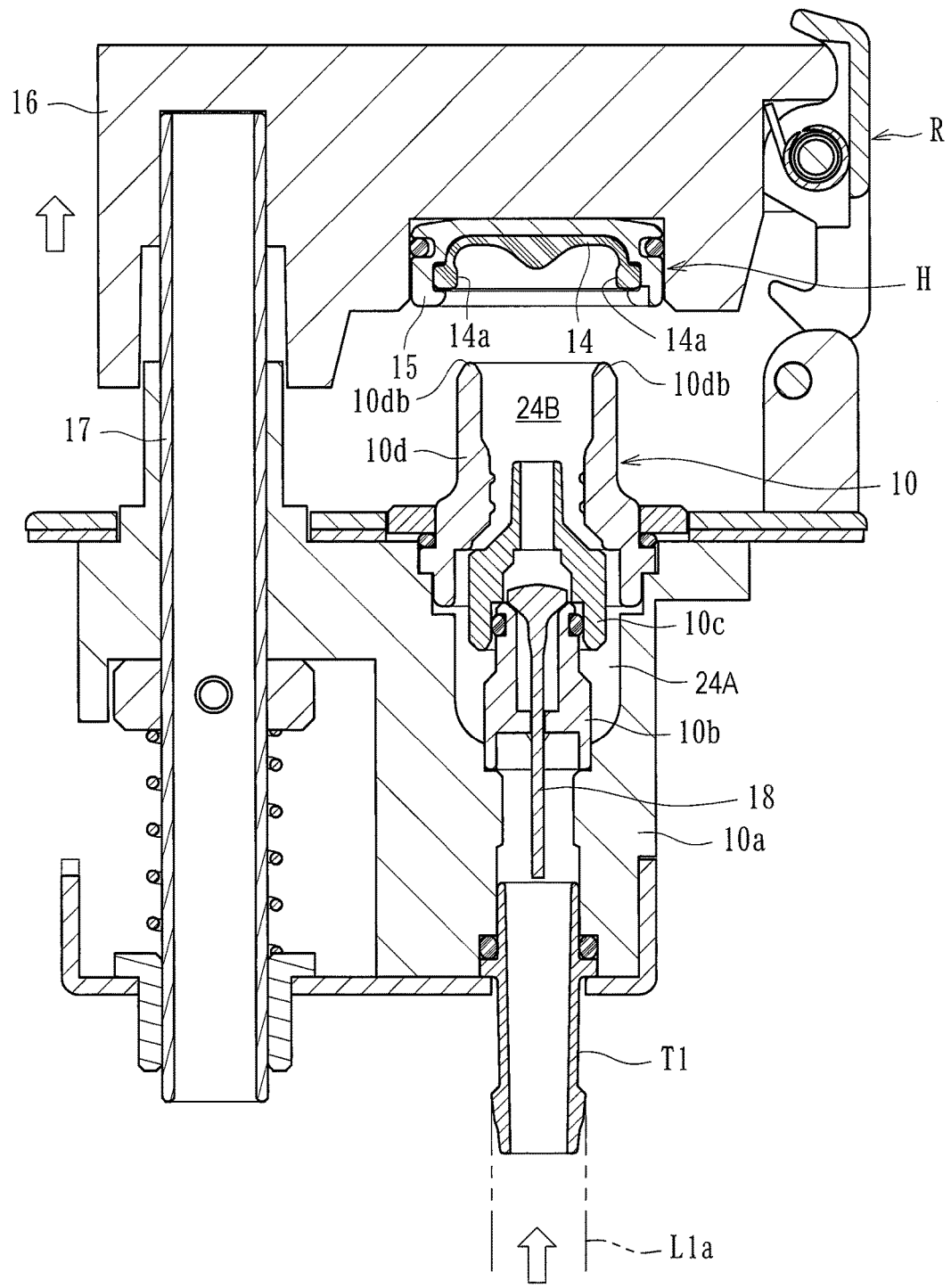

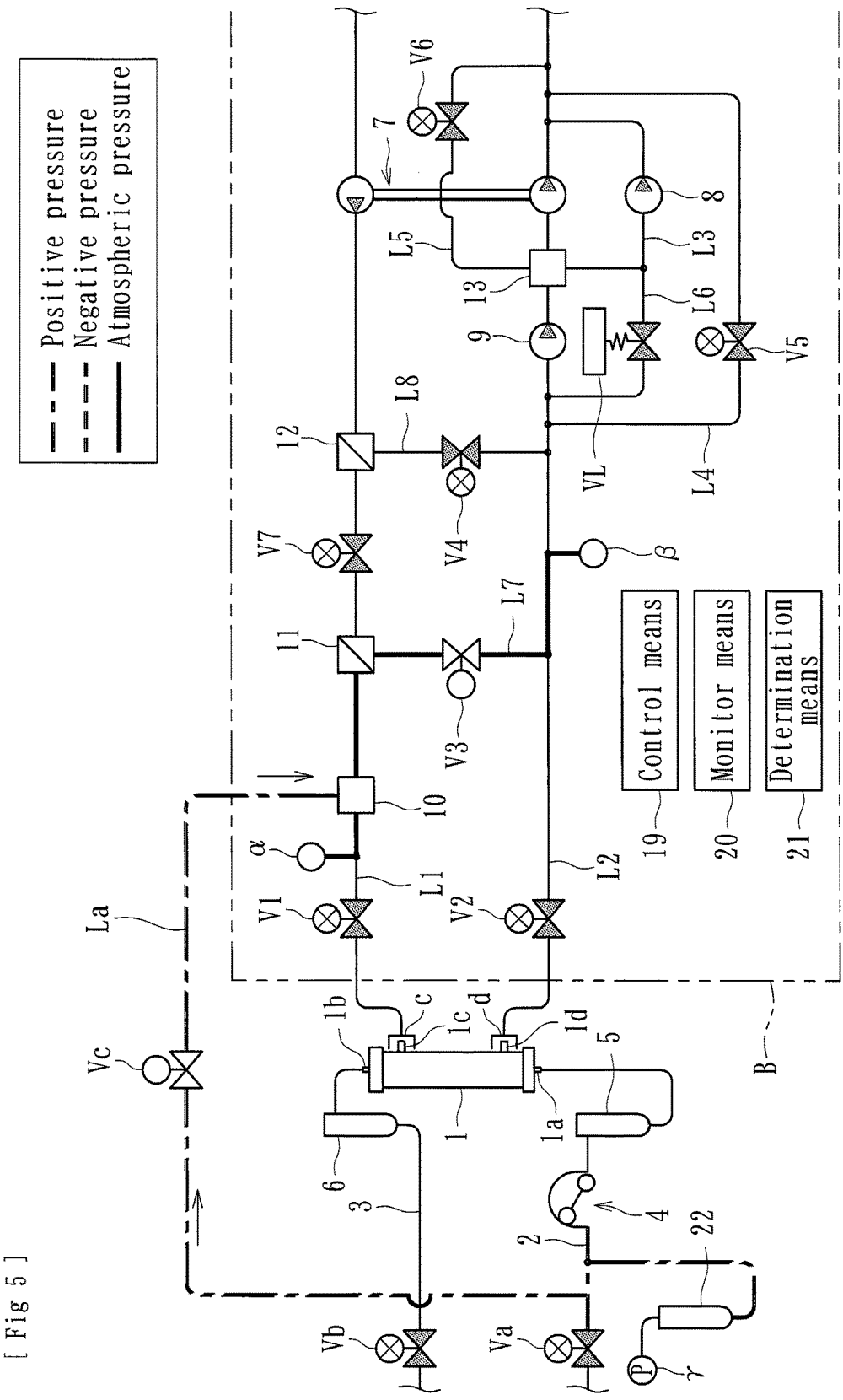
[Fig 5]

[Fig 6]
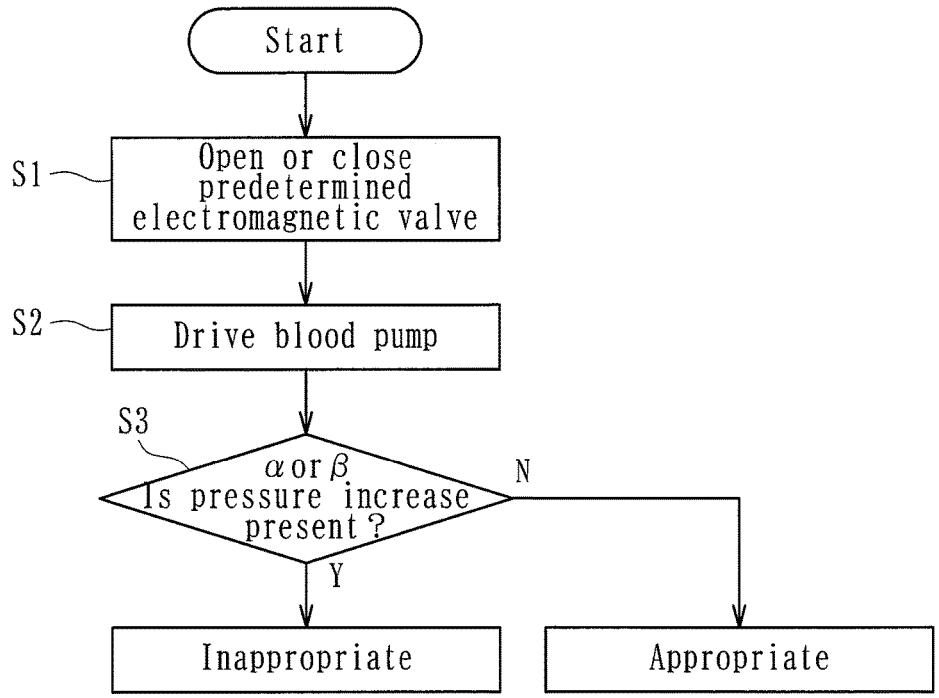
[Fig 7]
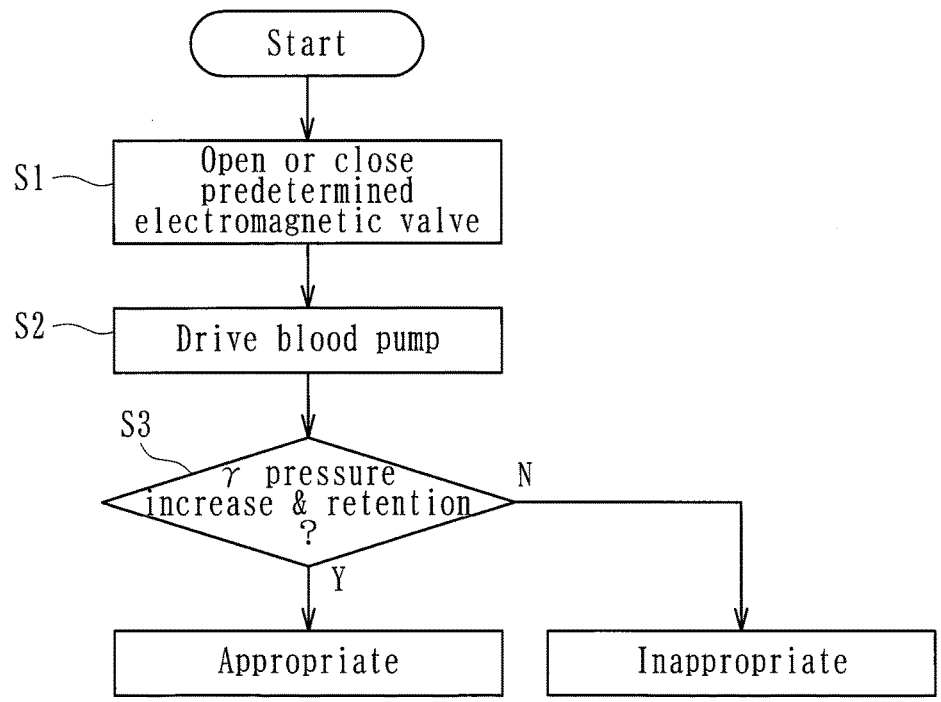

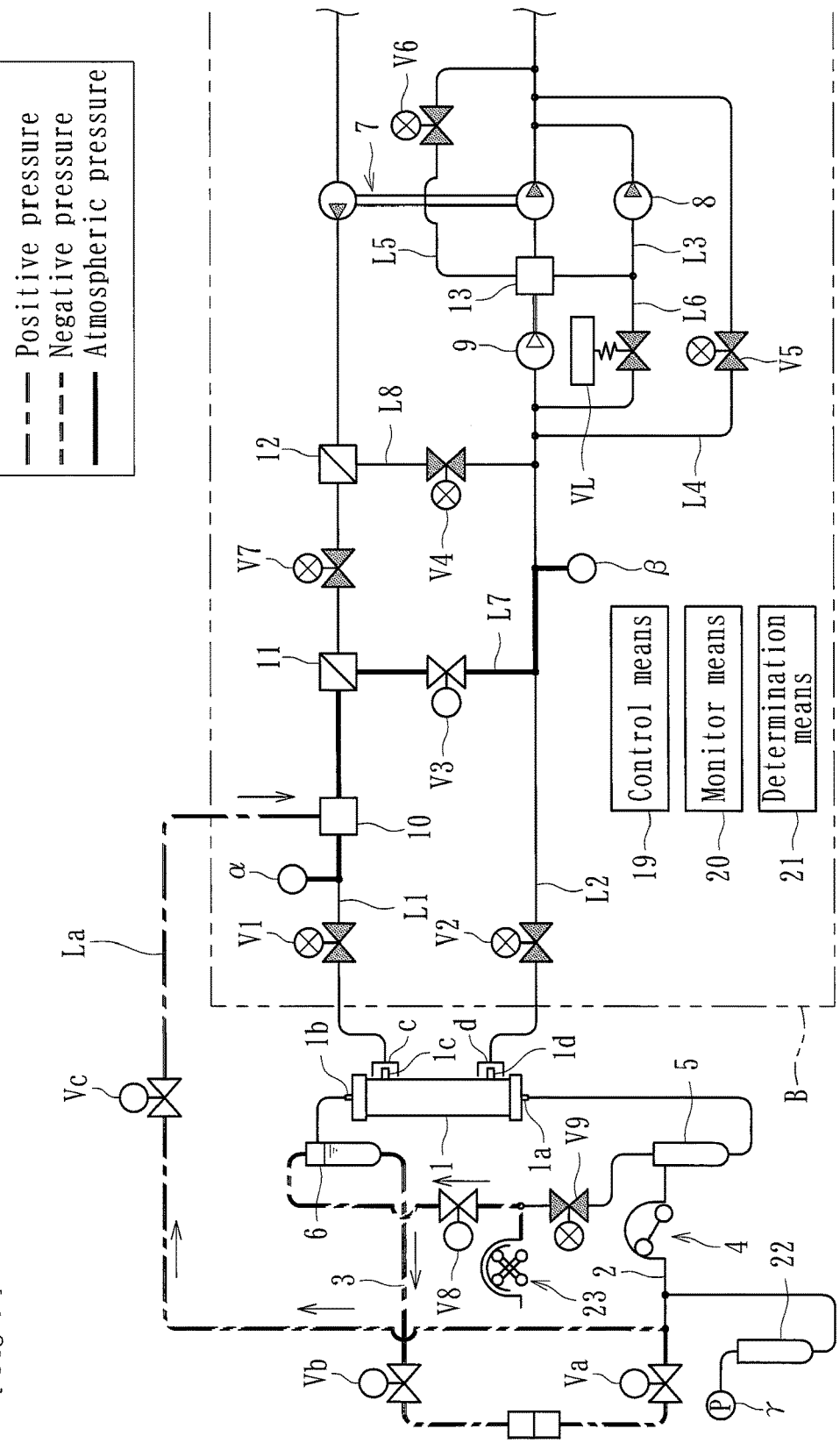
[Fig 8]

[Fig 9]
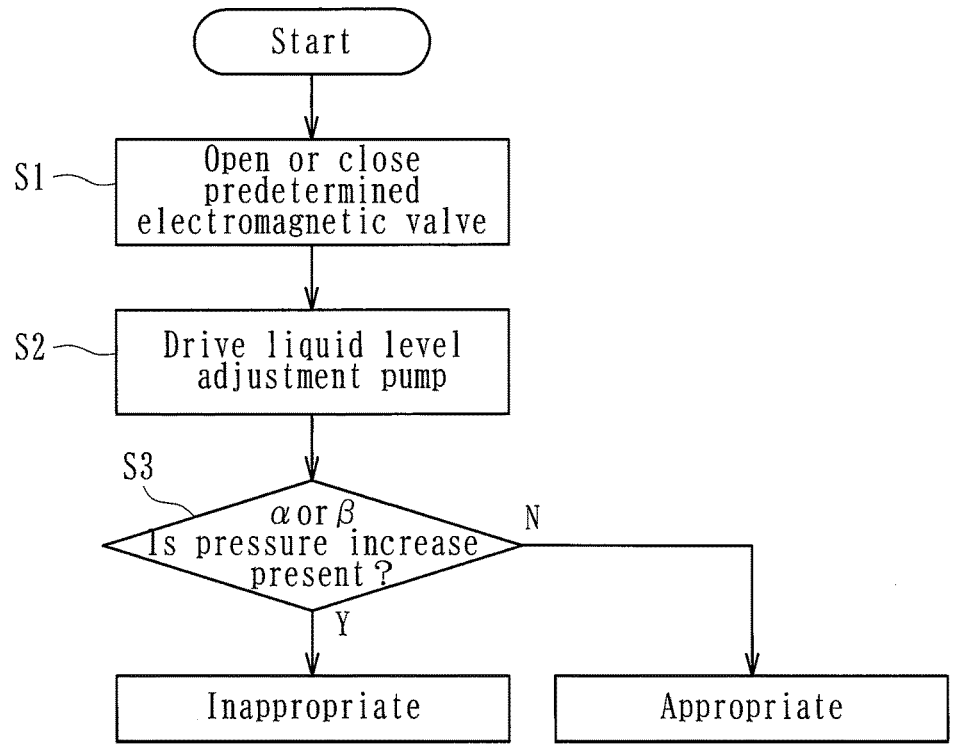
[Fig 10]
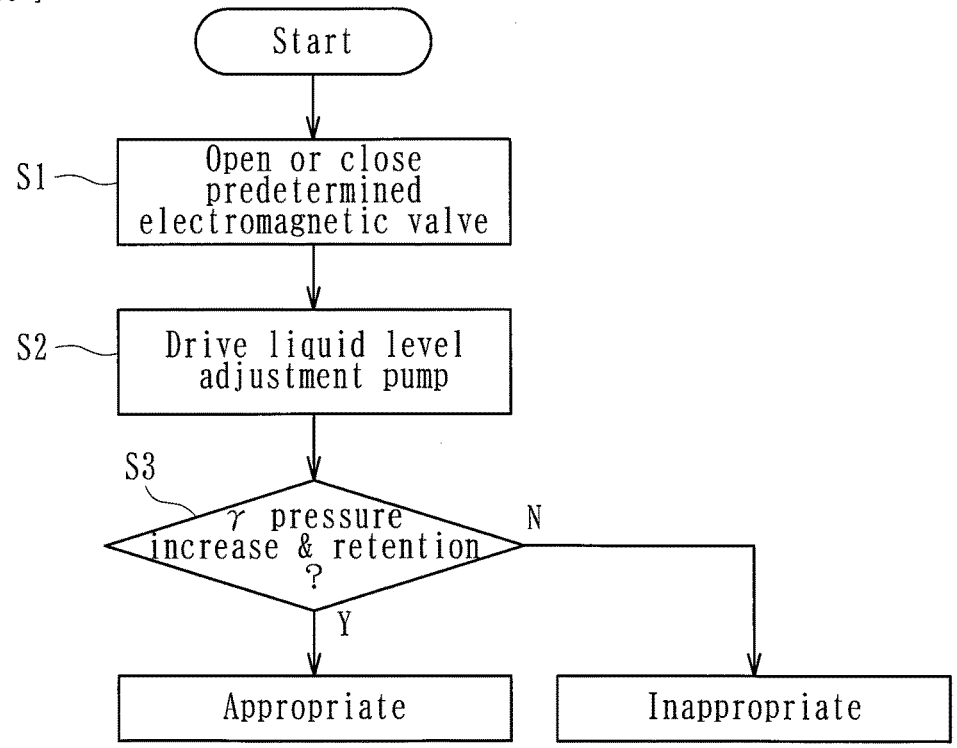

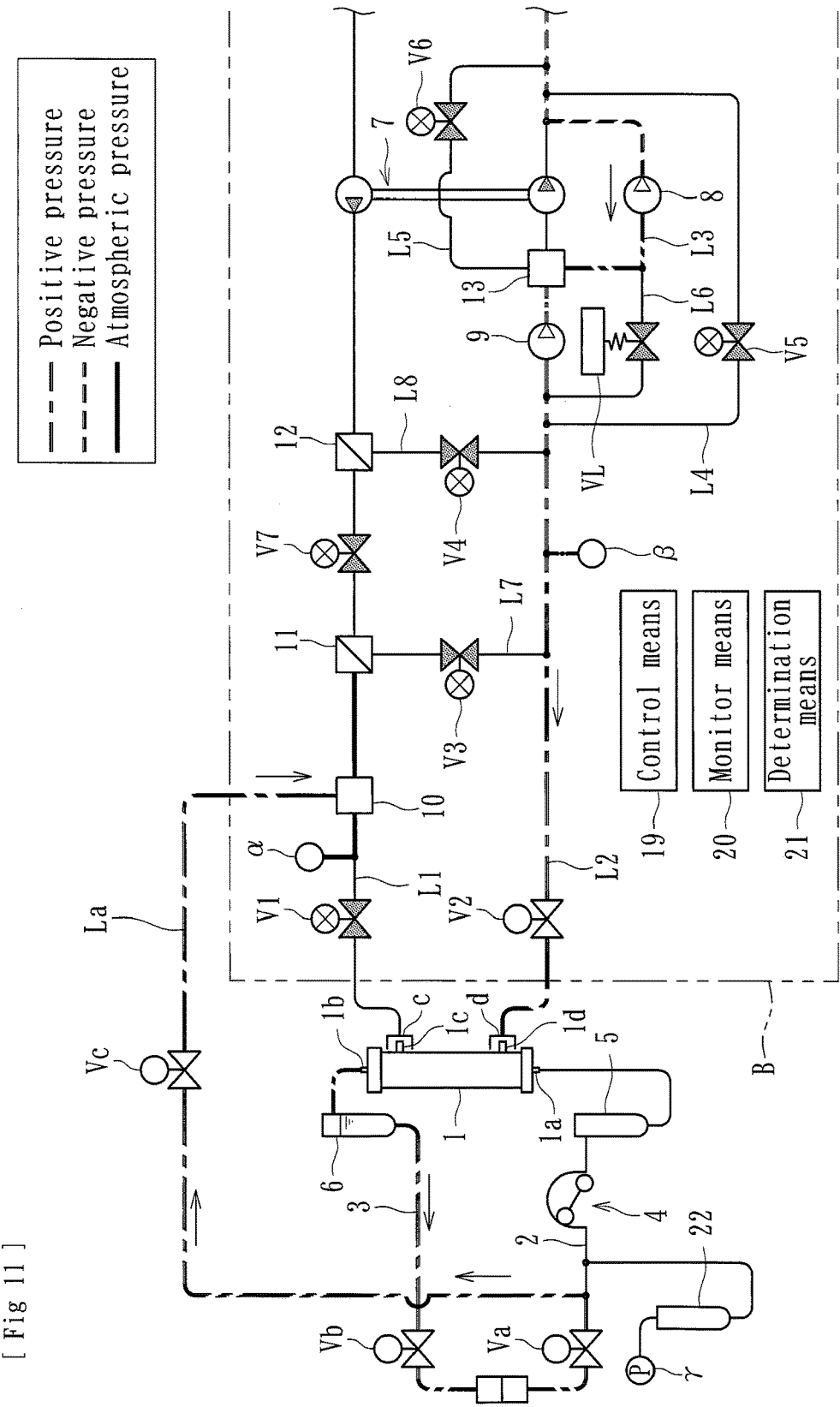
[Fig 11]

[Fig 12]
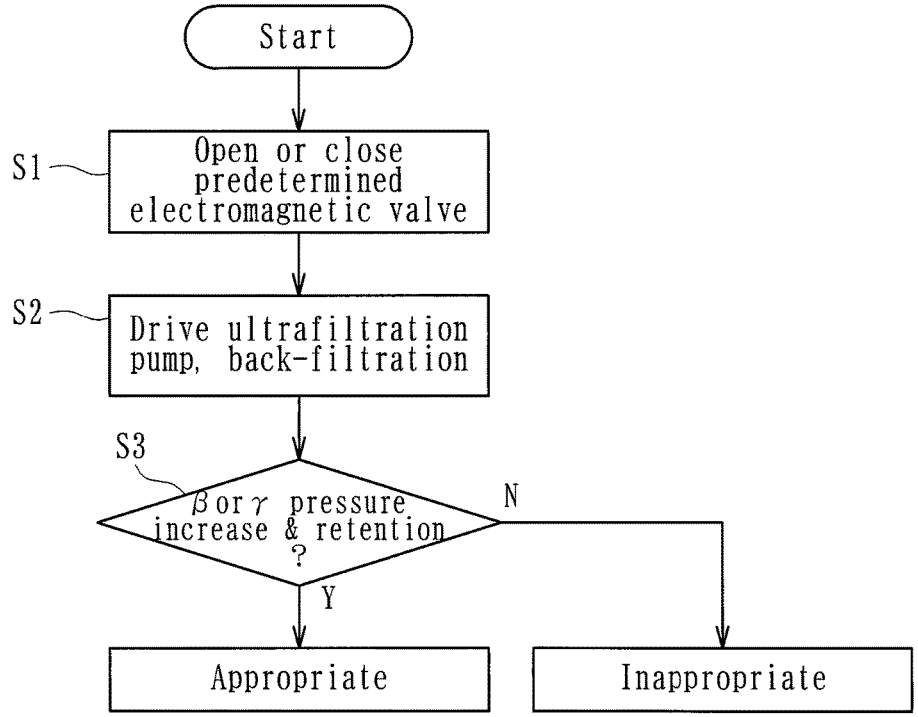
[Fig 13]
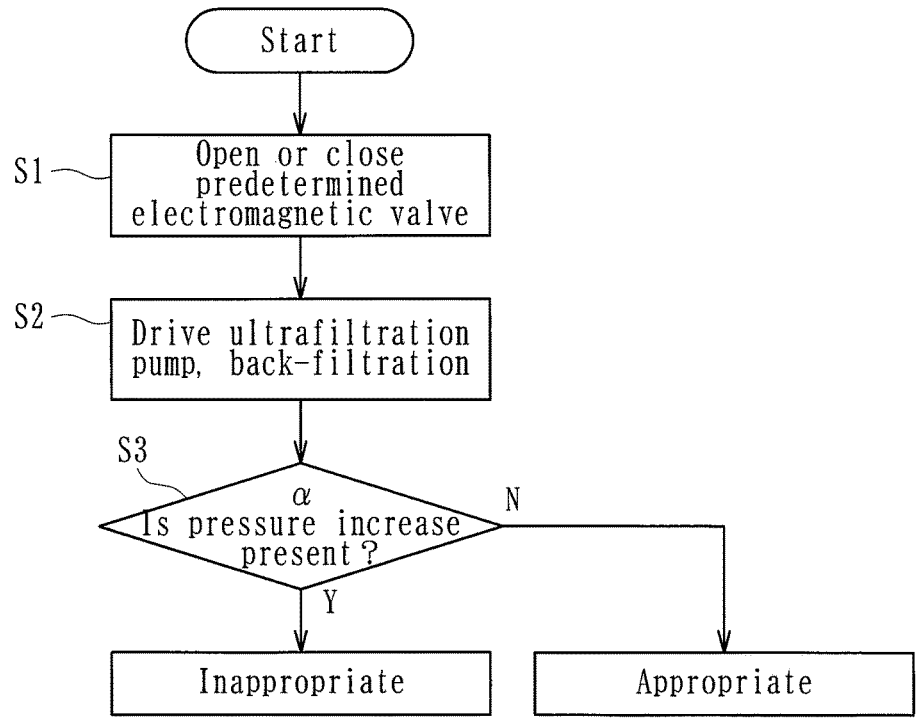

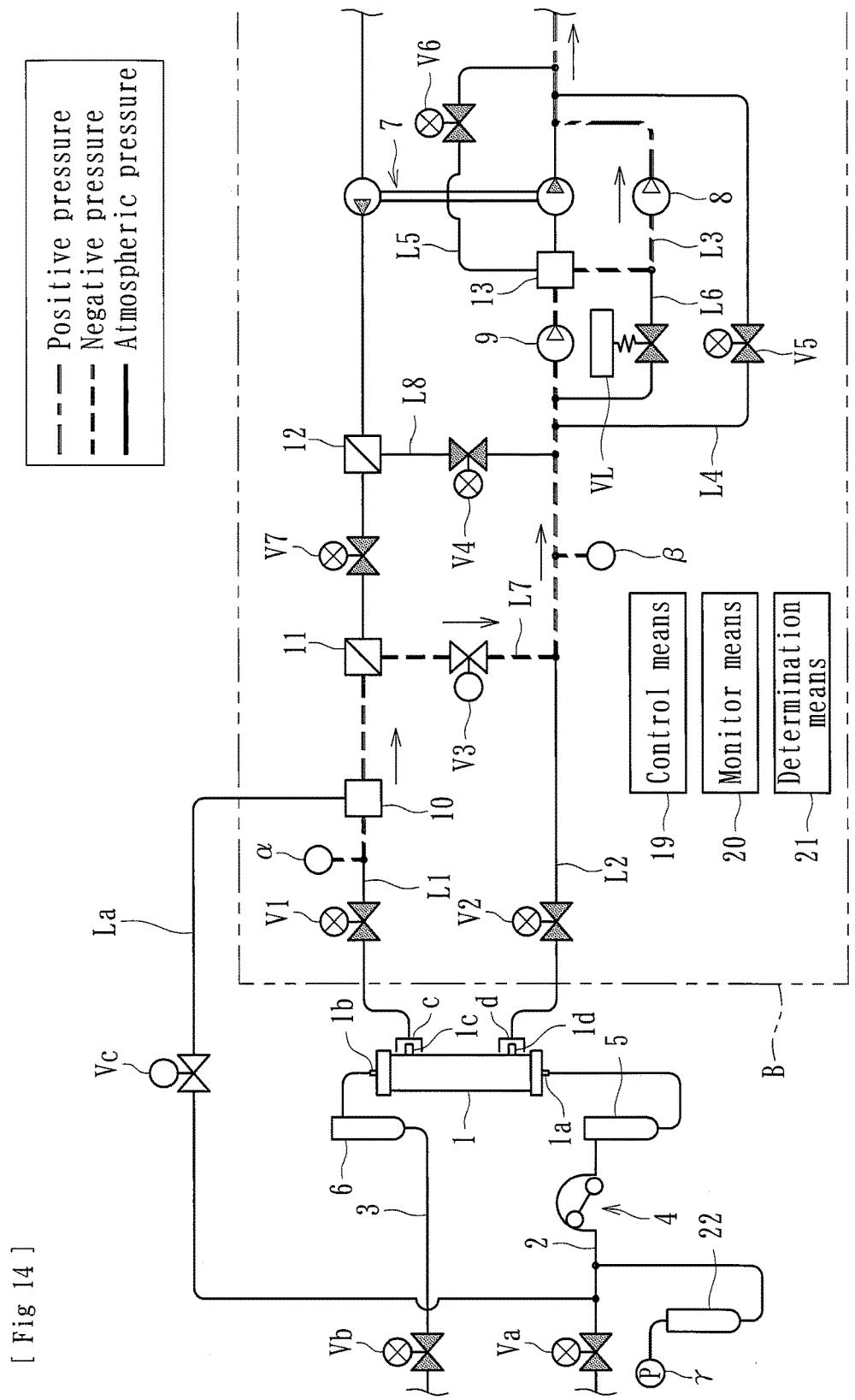
[Fig 14]

[Fig 15]
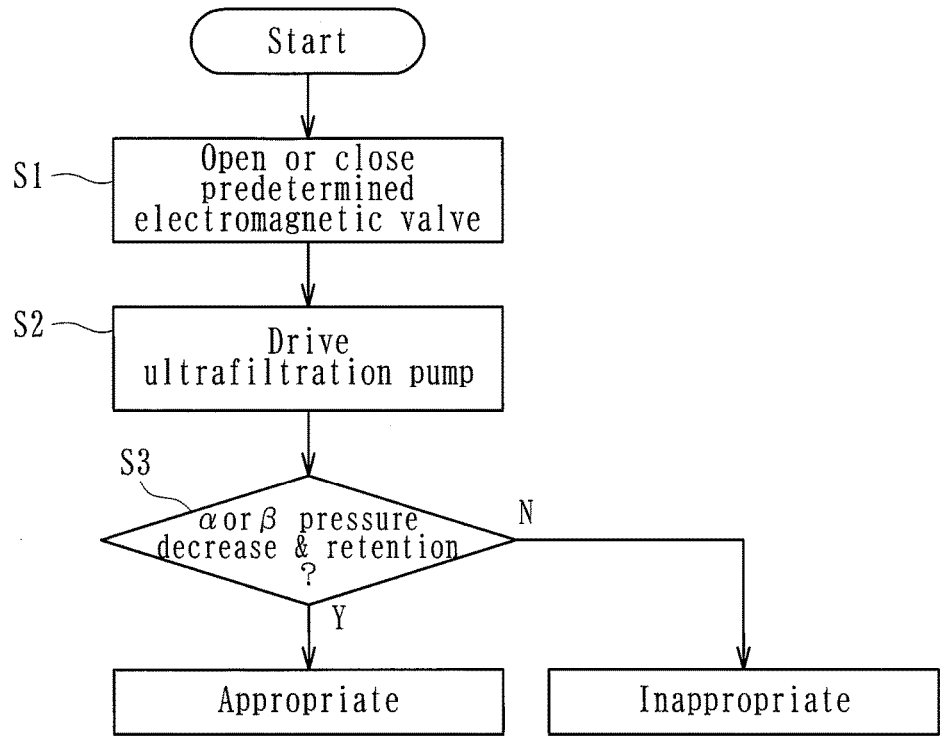
[Fig 16]
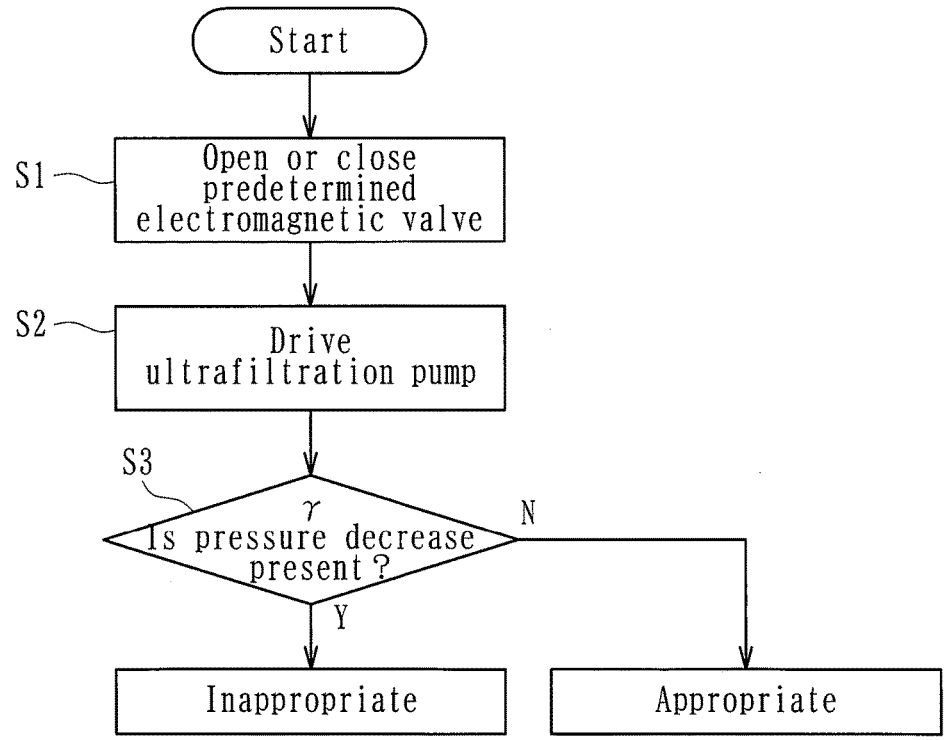

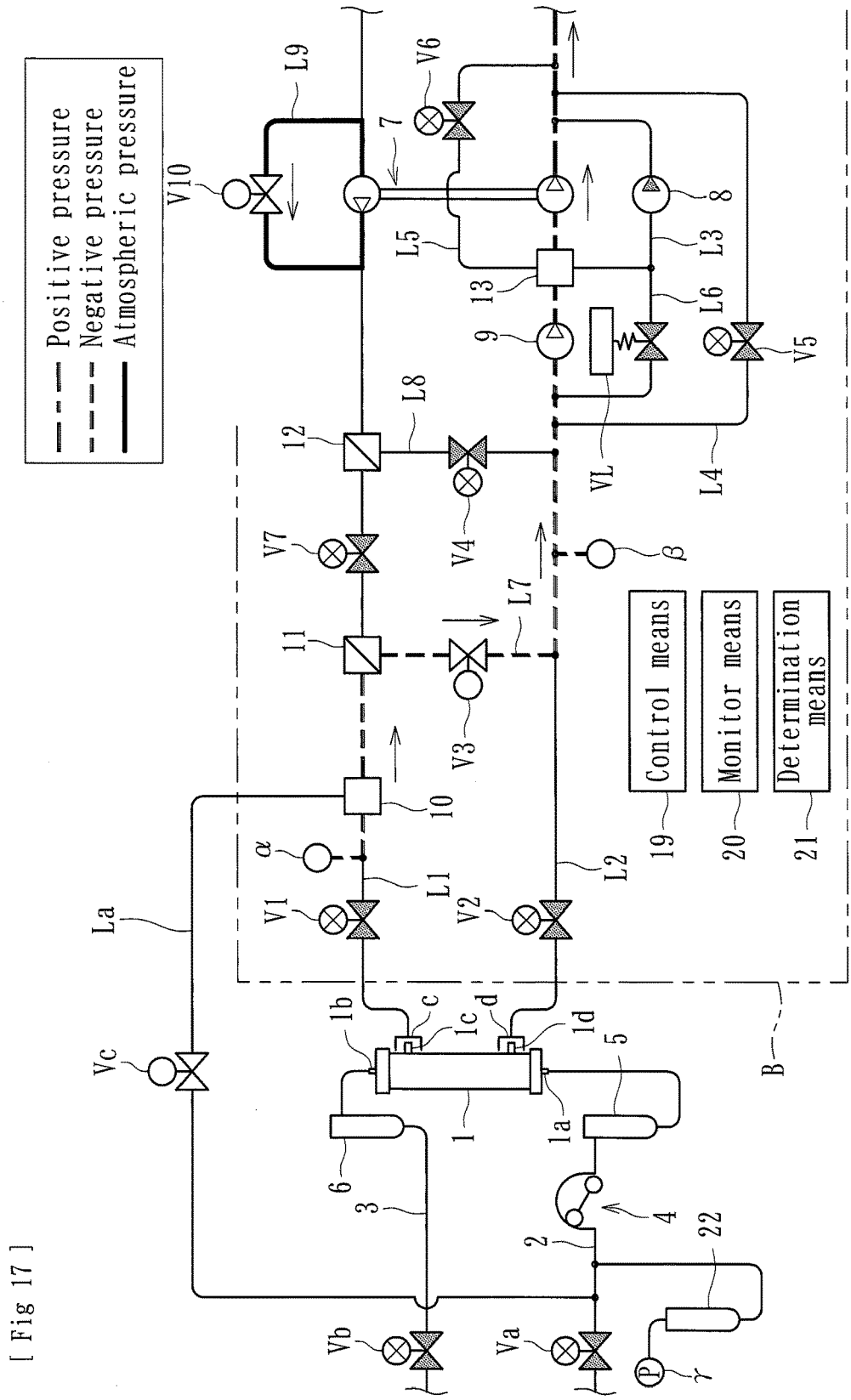
[Fig 17]

[ Fig 18 ]
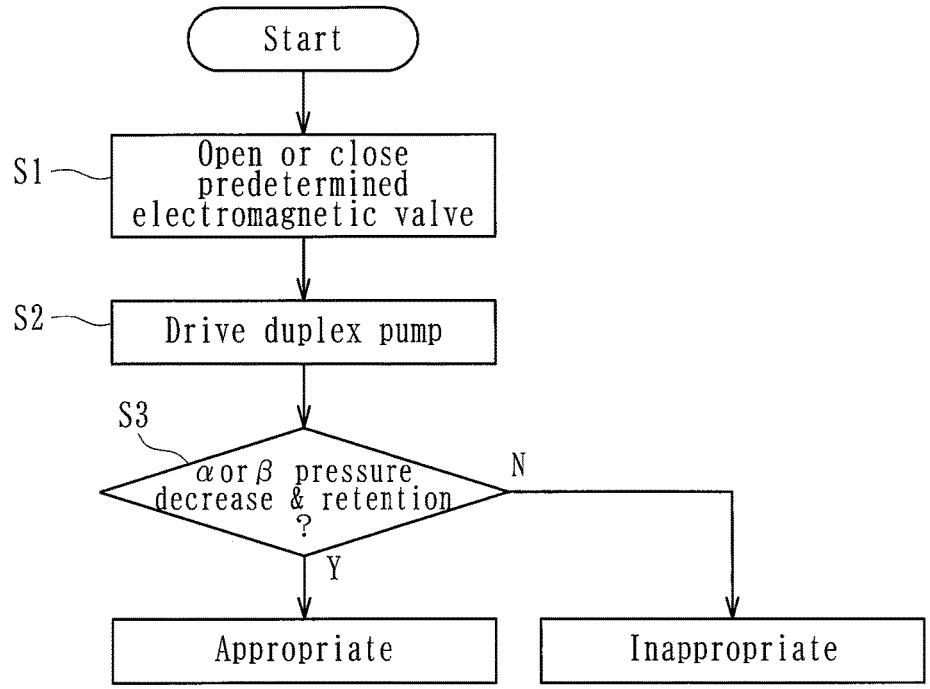
[ Fig 19 ]
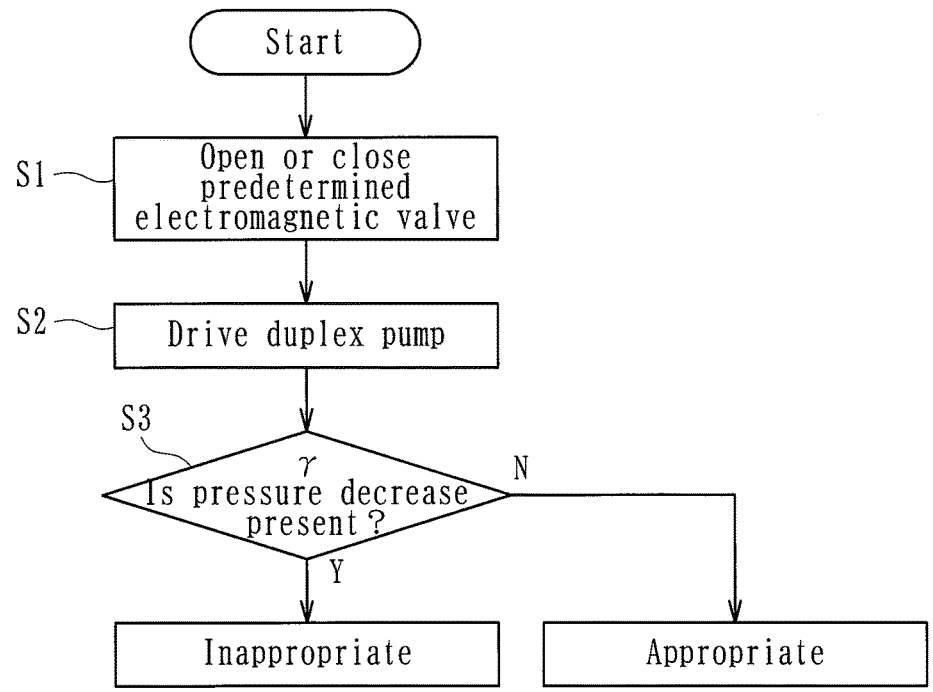

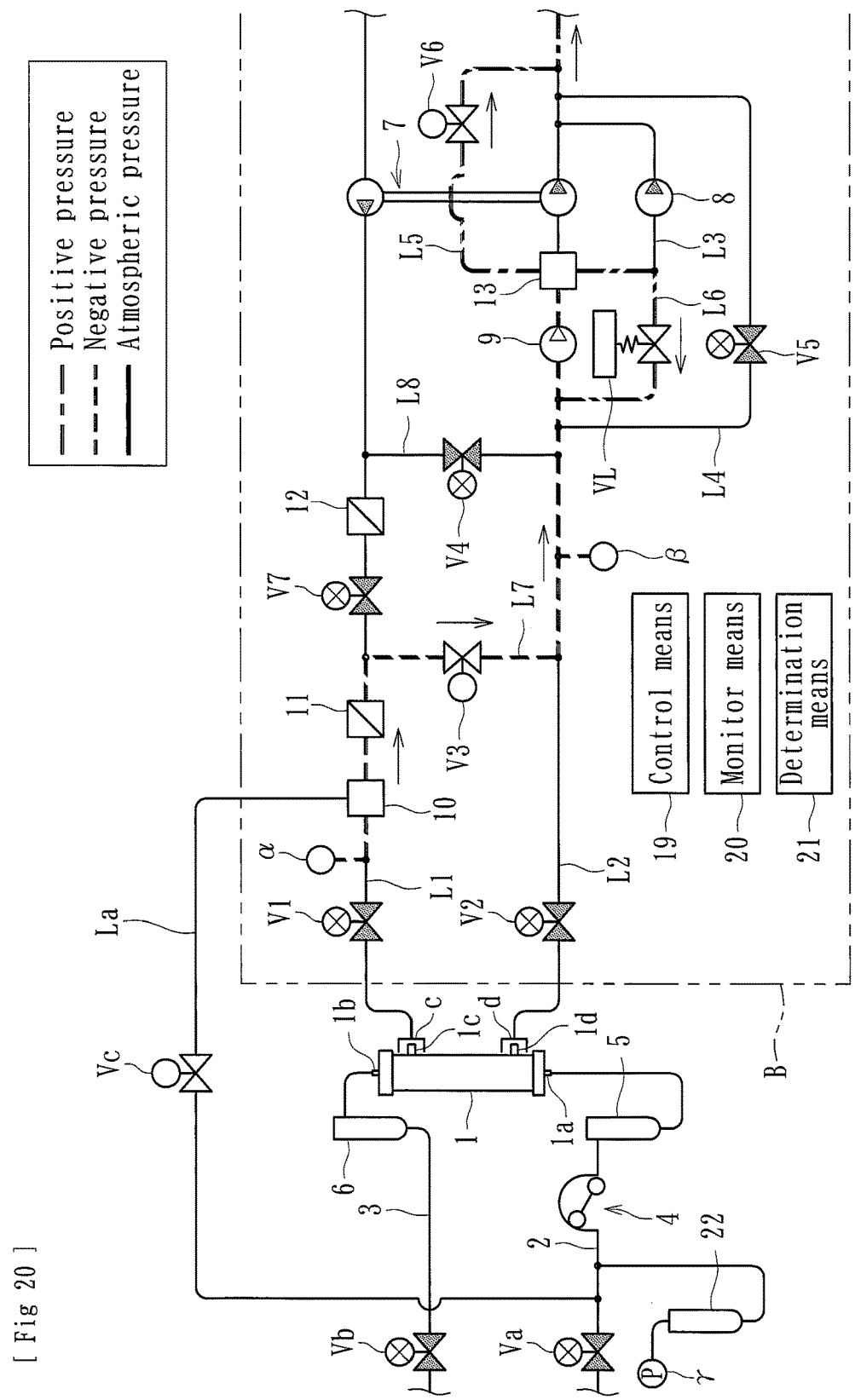
[Fig 20]

[Fig 21]
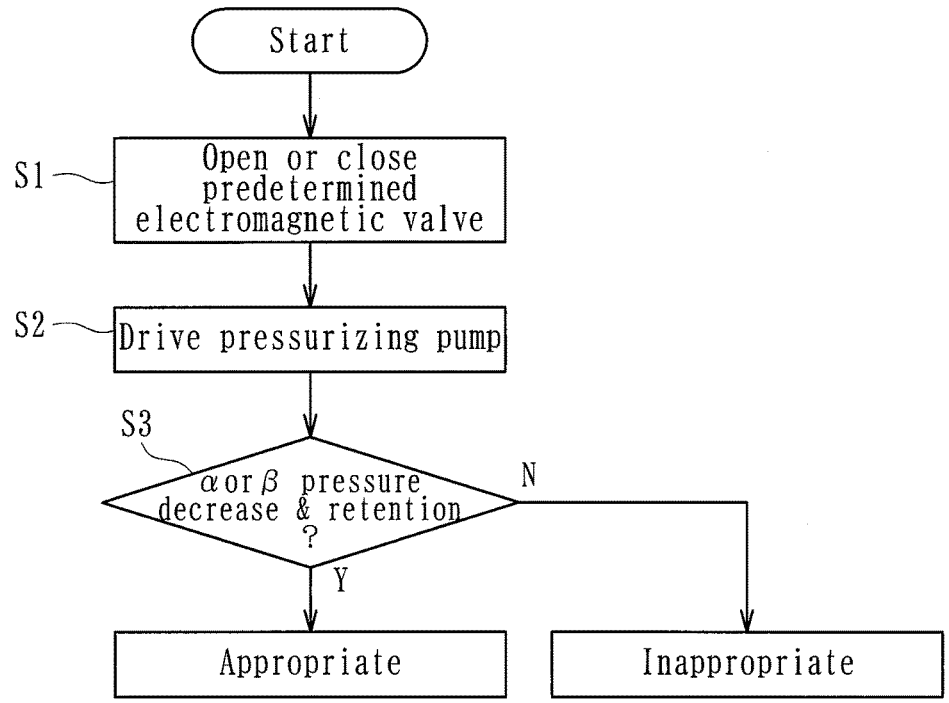
[Fig 22]
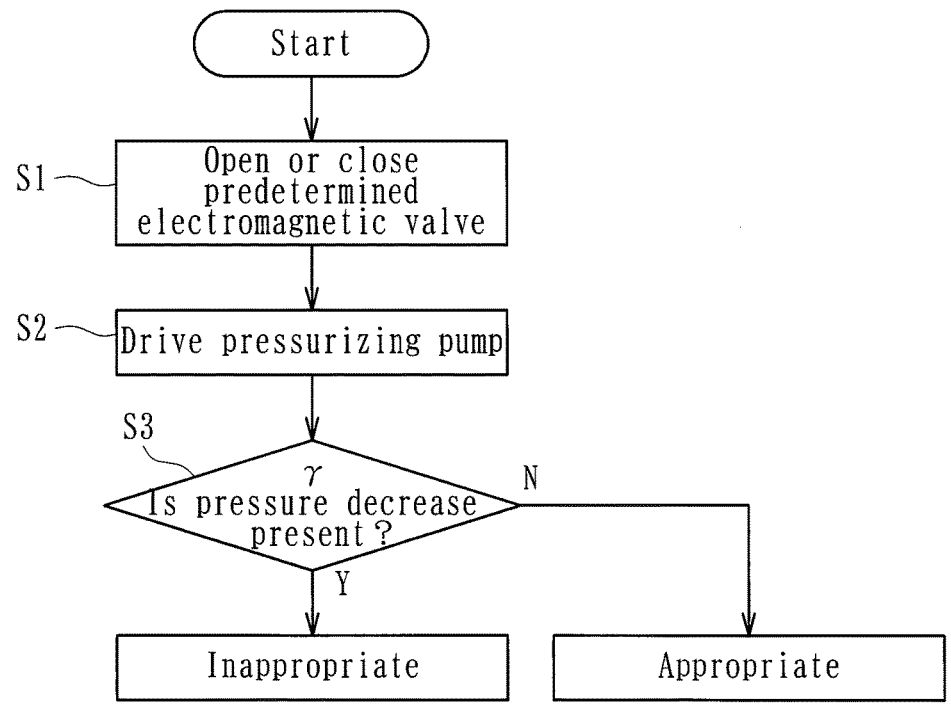

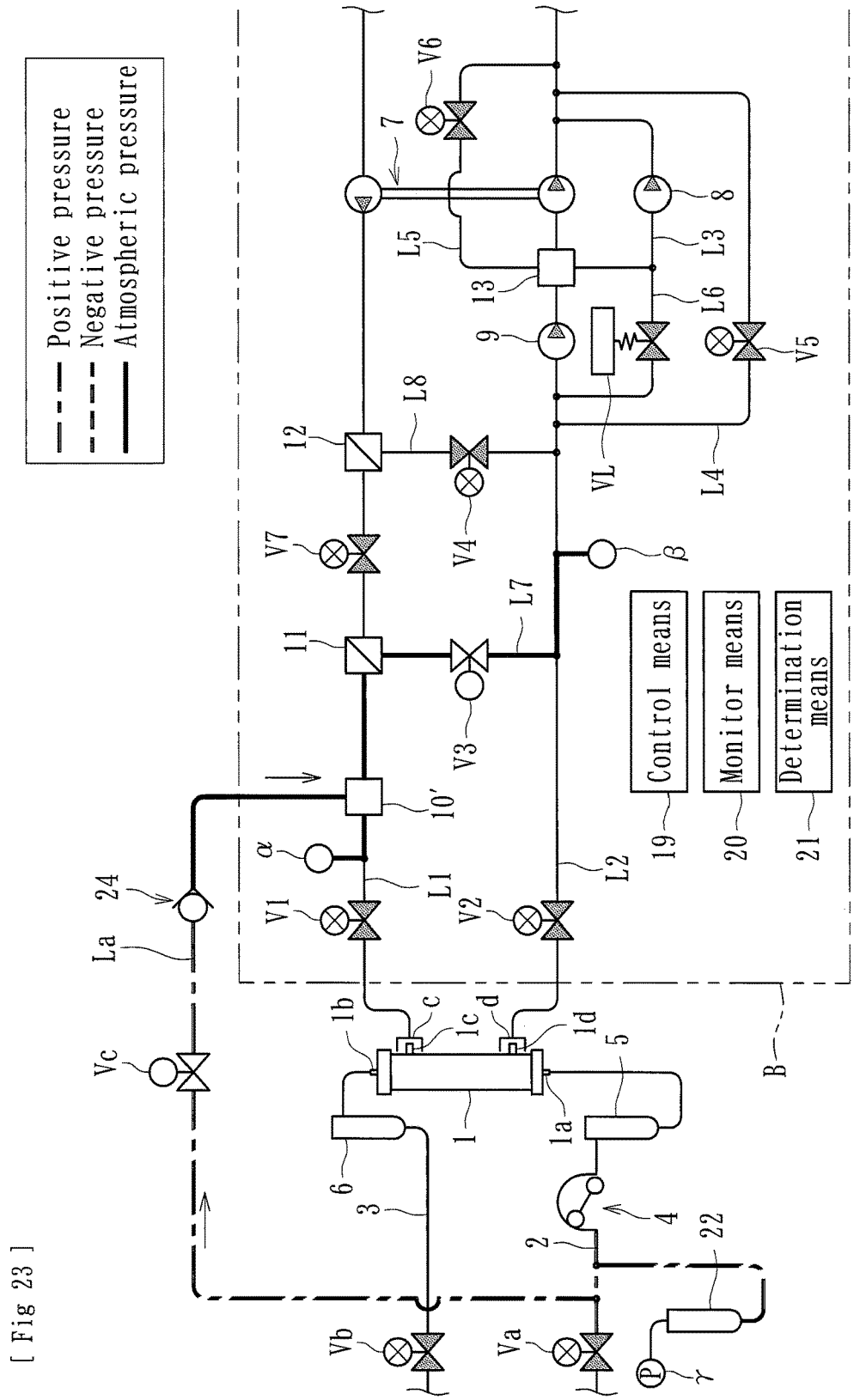
[Fig 23]

BLOOD PURIFICATION APPARATUS

FIELD

The present invention relates to a blood purification apparatus for extracorporeally circulating the blood of a patient to purify the blood.

BACKGROUND

In recent years, for a dialysis apparatus as a blood purification apparatus, there have been proposed a technology of priming, returning blood and substitution (emergency fluid infusion) using the dialysate to be supplied to a dialyzer at the time of dialysis treatment (particularly, online HDF or online HF) and a technology of utilizing the dialysate as substitution solution for online HDF or online HF treatment. For instance, PTL 1 discloses a dialysis apparatus including a dialysate supply line with one end connected to a dialysate extraction port (hereinafter referred to as an "extraction port") formed at a predetermined part of a dialysate introduction line and the other end connected to a blood circuit (an arterial blood circuit or a venous blood circuit); and a substitution pump disposed in the dialysate supply line. When priming, returning blood and substitution (emergency fluid infusion) is performed by such a dialysis apparatus, the dialysate of the dialysate introduction line can be supplied to the blood circuit (the arterial blood circuit or the venous blood circuit) by driving the substitution pump.

Normally, in a dialysate extraction device or a dialysate supply line in which a extraction port is formed, a check valve is disposed that allows a flow of liquid from the dialysate introduction line to the blood circuit and blocks a flow of liquid from the blood circuit to the dialysate introduction line. Such a check valve makes it possible to supply the dialysate of the dialysate introduction line to the blood circuit and to prevent blood flowing through the blood circuit from entering a pipe on the dialysis device side, such as the dialysate introduction line.

PTL 1: Japanese Unexamined Patent Application Publication No. 2004-313522

SUMMARY

However, in the conventional blood purification apparatus described above, it is not possible to determine before treatment whether or not the check valve functions effectively, that is disposed in a dialysate extraction device or a dialysate supply line in which a extraction port is formed (in particular, whether or not a flow of liquid from the blood circuit to the dialysate introduction line can be effectively blocked), and in the case where blocking of a flow of liquid is inappropriate due to a failure or the like, blood or the like flowing through the blood circuit may enter the dialysate introduction line side at the time of treatment.

The present teachings have been made in consideration of such a situation, and provides a blood purification apparatus that can easily and accurately determine before treatment whether or not blocking of liquid by a check valve is appropriate.

The present teachings provide a blood purification apparatus including: a blood circuit including an arterial blood circuit and a venous blood circuit for extracorporeally circulating blood of a patient; a blood purification device that is connected between the arterial blood circuit and the venous blood circuit, and that purifies the blood which flows through the blood circuit; a dialysate introduction line that introduces dialysate into the blood purification device and a dialysate discharge line that discharges dialysate from the blood purification device; a pressure detection device that is configured to detect a pressure in the dialysate introduction line or the dialysate discharge line, or a pressure in the blood circuit; a dialysate extraction device which is connected to the dialysate introduction line, and in which a extraction port through which the flowing dialysate is extractable is formed; a dialysate supply line with one end connected to the extraction port of the dialysate extraction device and the other end connected to the blood circuit, the dialysate supply line is configured to supply the dialysate of the dialysate introduction line to the blood circuit; and a check valve that is connected to the dialysate extraction device or the dialysate supply line, that allows a flow of liquid from the dialysate introduction line to the blood circuit and blocks a flow of liquid from the blood circuit to the dialysate introduction line, wherein the blood purification apparatus includes a control means that is configured to generate a pressure difference across the check valve between a side of the blood circuit and a side of the dialysate introduction line, a monitor means that is configured to monitor a change in a detection value of the pressure detection device based on the pressure difference, and a determination means that is configured to determine whether or not blocking of liquid by the check valve is appropriate based on the change in the detection value of the pressure detection device.

The present teachings provide the blood purification apparatus according to the teachings herein, wherein a blood pump for flowing liquid in the blood circuit is attached to the arterial blood circuit, and the control means drives the blood pump, thereby configured to generate a pressure difference across the check valve with the blood circuit side higher in pressure than the dialysate introduction line side.

The present teachings provide the blood purification apparatus according to the teachings herein, further comprising: an air trap chamber that is connected to the blood circuit, and that is for removing air in the liquid flowing in the blood circuit; and a liquid level adjustment pump for adjusting a liquid level by introducing air into an air layer of the air trap chamber or discharging air from an air layer of the air trap chamber, wherein the control means drives the liquid level adjustment pump, thereby configured to generate a pressure difference across the check valve with the blood circuit side higher in pressure than the dialysate introduction line side.

The present teachings provides the blood purification apparatus according to the teachings herein, wherein the control means back-filters the dialysate of the dialysate introduction line or the dialysate discharge line by the blood purification device, and introduces the dialysate into the blood circuit, thereby configured to generate a pressure difference across the check valve with the blood circuit side higher in pressure than the dialysate introduction line side.

The present teachings provide the blood purification apparatus according to the teachings herein, wherein the dialysate discharge line is connected to an ultrafiltration pump for performing ultrafiltration by removing water from the blood flowing in the blood purification device, and the control means drives the ultrafiltration pump, thereby configured to generate a pressure difference across the check valve with the dialysate introduction line side lower in pressure than the blood circuit side.

The present teachings provide the blood purification apparatus according to the teachings herein, further comprising a liquid delivery pump that is configured to introduce the dialysate into the dialysate introduction line and to discharge the dialysate from the dialysate discharge line into and from the blood purification device, wherein the control means drives the liquid delivery pump, thereby configured to generate a pressure difference across the check valve with the dialysate introduction line side lower in pressure than the blood circuit side.

The present teachings provide the blood purification apparatus according to the teachings herein, further comprising: a liquid delivery pump that is configured to introduce the dialysate into the dialysate introduction line and to discharge the dialysate from the dialysate discharge line into and from the blood purification device; a pressurizing pump or a circulating pump connected to the dialysate discharge line; and a detour line comprised of a flow path which branches between the pressurizing pump and the liquid delivery pump in the dialysate discharge line, and which makes a detour around the liquid delivery pump, wherein the control means drives the pressurizing pump or the circulating pump and causes the dialysate to flow through the detour line, thereby configured to generate a pressure difference across the check valve with the dialysate introduction line side lower in pressure than the blood circuit side.

According to the teachings herein, there are provided a control means that is configured to generate a pressure difference across the check valve between the blood circuit side and the dialysate introduction line side; a monitor means that is configured to monitor a change in a detection value of the pressure detection device based on the pressure difference; and a determination means that is configured to determine whether or not blocking of liquid by the check valve is appropriate based on the change in the detection value of the pressure detection device. Thus, it is possible to easily and accurately determine before treatment whether or not blocking of liquid by the check valve is appropriate.

According to the teachings herein, a blood pump for flowing liquid in the blood circuit is attached to the arterial blood circuit, and the control means drives the blood pump, thereby configured to generate a pressure difference across the check valve with the blood circuit side higher in pressure than the dialysate introduction line side. Thus, it is possible to easily and accurately determine before treatment whether or not blocking of liquid by the check valve is appropriate by utilizing the blood pump which is necessary at the time of treatment.

According to the teachings herein, there are provided an air trap chamber that is connected to the blood circuit, and that is for removing air in the liquid flowing in the blood circuit; and a liquid level adjustment pump for adjusting a liquid level by introducing air into an air layer of the air trap chamber or discharging air from an air layer of the air trap chamber, wherein the control means drives the liquid level adjustment pump, thereby configured to generate a pressure difference across the check valve with the blood circuit side higher in pressure than the dialysate introduction line side. Thus, it is possible to easily and accurately determine before treatment whether or not blocking of liquid by the check valve is appropriate by utilizing the liquid level adjustment pump which is necessary at the time of treatment.

According to the teachings herein, the control means back-filters the dialysate of the dialysate introduction line or the dialysate discharge line by the blood purification device, and introduces the dialysate into the blood circuit, thereby configured to generate a pressure difference across the check valve with the blood circuit side higher in pressure than the dialysate introduction line side. Thus it is possible to easily and accurately determine before treatment whether or not blocking of liquid by the check valve is appropriate by the back-filtering.

According to the teachings herein, the dialysate discharge line is connected to an ultrafiltration pump for performing ultrafiltration by removing water from the blood flowing in the blood purification device, and the control means drives the ultrafiltration pump, thereby configured to generate a pressure difference across the check valve with the dialysate introduction line side lower in pressure than the blood circuit side. Thus, it is possible to easily and accurately determine before treatment whether or not blocking of liquid by the check valve is appropriate by utilizing the ultrafiltration pump which is necessary at the time of treatment.

According to the teachings herein, there is further provided a liquid delivery pump that is configured to introduce the dialysate into the dialysate introduction line and to discharge the dialysate from the dialysate discharge line into and from the blood purification device, wherein the control means drives the liquid delivery pump, thereby configured to generate a pressure difference across the check valve with the dialysate introduction line side lower in pressure than the blood circuit side. Thus, it is possible to easily and accurately determine before treatment whether or not blocking of liquid by the check valve is appropriate by utilizing the liquid delivery pump which is necessary at the time of treatment.

According to the teachings herein, there are further provided a liquid delivery pump that is configured to introduce the dialysate into the dialysate introduction line and to discharge the dialysate from the dialysate discharge line into and from the blood purification device; a pressurizing pump or a circulating pump connected to the dialysate discharge line; and a detour line comprised of a flow path which branches between the pressurizing pump and the liquid delivery pump in the dialysate discharge line, and which makes a detour around the liquid delivery pump, wherein the control means drives the pressurizing pump or the circulating pump and causes the dialysate to flow through the detour line, thereby configured to generate a pressure difference across the check valve with the dialysate introduction line side lower in pressure than the blood circuit side. Thus, it is possible to easily and accurately determine before treatment whether or not blocking of liquid by the check valve is appropriate by utilizing the pressurizing pump or the liquid delivery pump which is necessary at the time of treatment.

BRIEF DESCRIPTION OF THE DRAWINGS

FIG. 1 is a schematic diagram illustrating a blood purification apparatus according to an embodiment of the present invention.

FIG. 2 is a sectional schematic diagram illustrating a dialysate extraction apparatus (with an opening and closing device attached to an extraction port) in the blood purification apparatus.

FIG. 3 is a sectional schematic diagram illustrating the dialysate extraction apparatus (with an opening and closing device attached to the extraction port).

FIG. 4 is a sectional schematic diagram illustrating the dialysate extraction apparatus (with an opening and closing device removed from the extraction port).

FIG. 5 is a schematic diagram illustrating an operation (operation by driving a blood pump) of the blood purification apparatus.

FIG. 6 is a flow chart illustrating details of control in the blood purification apparatus.

FIG. 7 is a flow chart illustrating details of other control in the blood purification apparatus.

FIG. 8 is a schematic diagram illustrating an operation (operation by driving a liquid level adjustment pump) of the blood purification apparatus.

FIG. 9 is a flow chart illustrating details of control in the blood purification apparatus.

FIG. 10 is a flow chart illustrating details of other control in the blood purification apparatus.

FIG. 11 is a schematic diagram illustrating an operation (operation by back-filtration) of the blood purification apparatus.

FIG. 12 is a flow chart illustrating details of control in the blood purification apparatus.

FIG. 13 is a flow chart illustrating details of other control in the blood purification apparatus.

FIG. 14 is a schematic diagram illustrating an operation (operation by driving an ultrafiltration pump) of the blood purification apparatus.

FIG. 15 is a flow chart illustrating details of control in the blood purification apparatus.

FIG. 16 is a flow chart illustrating details of other control in the blood purification apparatus.

FIG. 17 is a schematic diagram illustrating an operation (operation by driving a duplex pump) of the blood purification apparatus.

FIG. 18 is a flow chart illustrating details of control in the blood purification apparatus.

FIG. 19 is a flow chart illustrating details of other control in the blood purification apparatus.

FIG. 20 is a schematic diagram illustrating an operation (operation by driving a pressurizing pump) of the blood purification apparatus.

FIG. 21 is a flow chart illustrating details of control in the blood purification apparatus.

FIG. 22 is a flow chart illustrating details of other control in the blood purification apparatus.

FIG. 23 is a schematic diagram illustrating a blood purification apparatus according to another embodiment of the present invention.

DETAILED DESCRIPTION

Hereinafter, an embodiment of the present invention will be specifically described with reference to the drawings. A blood purification apparatus according to the present embodiment is used for blood purification treatment (hemodialysis treatment) that extracorporeally circulates the blood of a patient to be able to purify the blood. As illustrated in FIG. 1, the blood purification apparatus mainly includes a blood circuit in which an arterial blood circuit 2 and a venous blood circuit 3 are connected to a dialyzer 1 (blood purification device), and a dialysis device B having a dialysate introduction line L1 and a dialysate discharge line L2.

The dialyzer 1 is for purifying blood, and is connected via ports 1a, 1b to the arterial blood circuit 2 and the venous blood circuit 3, respectively included in the blood circuit, and is connected to the dialysate introduction line L1 and the dialysate discharge line L2 via ports 1c, 1d, respectively. A blood pump 4 comprised of a peristaltic pump is disposed in the arterial blood circuit 2, and it is possible to deliver liquid such as dialysate in the blood circuit by driving the blood pump 4.

Also, an arterial puncture needle (a) and a venous puncture needle (b) are attachable to the leading end of the arterial blood circuit and the leading end of the venous blood circuit, respectively. It is designed that driving the blood pump 4 with the arterial puncture needle (a) and the venous puncture needle (b) punctured in a patient causes the blood of the patient collected through the arterial puncture needle a to be extracorporeally circulated in the blood circuit, and after blood purification and ultrafiltration are performed by the dialyzer 1, the blood is returned to the patient through the venous puncture needle (b).

In addition, on the upstream side (between the blood pump 4 and a clamp device Va) of the blood pump 4 in the arterial blood circuit 2, a pressure detection device (γ), which can detect a pressure (liquid pressure) of a portion of the side and can measure a removed blood pressure at the time of treatment, is connected via a chamber 22. It is to be noted that an air trap chamber 5 is connected to the arterial blood circuit 2 and the clamp device Va is disposed in the leading end side, and an air trap chamber 6 is connected to the venous blood circuit 3 and a clamp device Vb is disposed in the leading end side.

Furthermore, the dialysate introduction line L1 and the dialysate discharge line L2 are connected to a duplex pump 7 as a liquid delivery pump, which supplies dialysate prepared at a predetermined concentration to the dialyzer 1 and causes the dialysate to be discharged from the dialyzer 1. Specifically, the duplex pump 7 is disposed to straddle the dialysate introduction line L1 and the dialysate discharge line L2, and a configuration is adopted in which driving the duplex pump 7 allows dialysate to be introduced via the dialysate introduction line L1 and dialysate to be discharged via the dialysate discharge line L2 into and from the dialyzer 1.

Also, filters 11, 12 are connected to the dialysate introduction line L1, the dialysate introduced into the dialyzer 1 can be filtered by the filters 11, 12, and a flow path can be blocked or opened by electromagnetic valves V1, V7 at any timing. On the upstream side (between the electromagnetic valve V1 and the dialysate extraction device 10) of the electromagnetic valve V1 in the dialysate introduction line L1, a pressure detection device (a) is connected, comprised of a sensor that can detect a pressure (liquid pressure in a flow path) in a flow path. It is to be noted that the dialysate introduction line L1 is connected to the dialysate discharge line L2 via bypass lines L7, L8, and these bypass lines L7, L8 are connected to electromagnetic valves V3, V4, respectively.

Also, the dialysate discharge line L2 is connected to detour lines L3, L4 to make a detour around the duplex pump 7, and an ultrafiltration pump 8 is connected to the detour line L3. Thus, it is designed that driving the ultrafiltration pump 8 in a process of extracorporeally circulating the blood of a patient in the blood circuit allows water in the blood flowing through the dialyzer 1 to be removed. Furthermore, on the upstream side (the left side in FIG. 1) of the duplex pump 7 in the dialysate discharge line L2, a pressurizing pump 9 is connected, that makes liquid pressure adjustment of the dialysate discharge line L2 in the duplex pump 7 (the liquid delivery pump), and a detour line L5 is extended via a chamber 13 from between the pressurizing pump 9 and the duplex pump 7.

In addition, on the downstream side (between a connection portion of the bypass line L7 and a connection portion of the bypass line L8) of the electromagnetic valve V2 in the dialysate discharge line L2, a pressure detection device (β) is connected, comprised of a sensor that can detect a pressure (liquid pressure in a flow path) in a flow path. Furthermore, the dialysate discharge line L2 and the detour lines L4, L5 branched therefrom are connected to electromagnetic valves V2, V5, V6, and a flow path can be blocked or opened at any timing. It is to be noted that a detour line L6 is extended to the detour line L3 from between a connecting portion of the detour line L4 in the dialysate discharge line L2 and the pressurizing pump 9, and a relief valve VL is connected to the detour line L6.

The dialysate introduction line L1 according to the present embodiment is connected to a dialysate extraction apparatus that can extract the dialysate flowing through the dialysate introduction line L1. As illustrated in FIGS. 2 to 4, the dialysate extraction apparatus is connected to the flow path (dialysate introduction line L1) for dialysate, and is configured to include a dialysate extraction device 10, in which a extraction port 10d through which the flowing dialysate is extractable, is formed; and an opening and closing device H which is attachable and detachable to the dialysate extraction device 10 to allow the extraction port 10d to be opened and closed, and in which a seal section 14a for sealing in a closed state of the extraction port 10d is formed.

The dialysate extraction device 10 is configured to include a first extraction member 10a connected to the dialysate introduction line L1, a second extraction member 10b formed in the first extraction member 10a, a third extraction member 10c which is assembled to the second extraction member 10b and in which a flow path is formed, and a extraction port 10d attached so as to cover the third extraction member 10c. The extraction port 10d is comprised of a port-shaped part connected to one end of a dialysate supply line La (see FIG. 1), and has an insertion hole for inserting a connector (not illustrated) formed at the one end of the dialysate supply line La, and a female thread part into which the connector can be screwed. Also, the extraction port 10d is removable from the connector.

The dialysate supply line La has one end connected to the extraction port 10d of the dialysate extraction device 10 and the other end connected to the blood circuit (the arterial blood circuit 2 in the present embodiment). The dialysate supply line La is comprised of a flow path which allows the dialysate of the dialysate introduction line L1 to be supplied to the blood circuit. The dialysate supply line La is connected to a clamp device Vc, and the clamp device Vc is designed to allow opening or closing at any timing. It is to be noted that although the other end of the dialysate supply line La is connected to the arterial blood circuit 2 in the present embodiment, the other end may be connected to another part (for instance, the venous blood circuit 3, or the air trap chamber 5, the air trap chamber 6) of the blood circuit.

On the other hand, in the first extraction member 10a of the dialysate extraction device 10, an inlet port T1 and an outlet port T2 are each formed, and the inlet port T1 and the outlet port T2 are connected to an inlet end L1a and an outlet end L1b, respectively in the dialysate introduction line L1. Also, a flow path of liquid in communication with the inlet port T1 is formed in the inside of the second extraction member 10b and the third extraction member 10c, and a check valve 18 is disposed in the flow path. The check valve 18 allows flow (an upward flow in FIGS. 2, 4) of liquid from the dialysate supply line La to the blood circuit, and blocks flow (a downward flow in FIGS. 2, 4) of liquid from the blood circuit to the dialysate introduction line L1.

The leading end of the third extraction member 10c is open in the extraction port 10d, and liquid flowing through the internal flow path of the second extraction member 10b and the third extraction member 10c is designed to reach the extraction port 10d. In addition, a space 24B allowing a flow of liquid is formed between the third extraction member 10c and the opening and closing device H, and the space 24B communicates with a space 24A which is formed in the first extraction member 10a. In other words, a gap having a predetermined dimension is formed between the outer circumferential surface of the third extraction member 10c and the inner circumferential surface of the extraction port 10d, and the space 24A and the space 24B communicate with each other via the gap.

The space 24B is connected to the outlet port T2, and the liquid in the space 24B is designed to flow to the dialysate introduction line L1 via the outlet port T2. Thus, a configuration is adopted in which with the opening and closing device H removed from the dialysate extraction device 10, the dialysate introduced from the introduction port T1 is discharged through the extraction port 10d via the internal flow path of the second extraction member 10b and the third extraction member 10c, and is supplied to the blood circuit via the dialysate supply line La, and with the opening and closing device H attached to the dialysate extraction device 10, the dialysate introduced through the introduction port T1 flows into the spaces 24B, 24A, and returns to the dialysate introduction line L1 via the outlet port T2.

Also, the opening and closing device H according to the present embodiment includes a seal member 14 in which the seal section 14a is partially formed and which is composed of a flexible member such as a resin material and a rubber material; and a cap member 15 that covers and holds the seal member 14, the cap member 15 being composed of, for instance, a hard resin. The seal member 14 and the cap member 15 are integrated. In the edge of the seal member 14, the seal section 14a is formed that comes into contact with the outer circumferential surface of the extraction port 10d for sealing.

With the opening and closing device H attached to the extraction port 10d, external leakage of the dialysate flowing through the dialysate introduction line L1 is prevented by the seal member 14, and cleaning liquid or sterilizing liquid flowing through the dialysate introduction line L1 reaches a tip end of the extraction port 10d and the tip end 10db and its vicinity (an area facing a space Y between the seal section 14a and the tip end 10db) is designed to be cleaned or sterilized. It is to be noted that a projection section 14b projecting toward the extraction port 10d side is formed in the center of the surface of the seal member 14, facing the extraction port 10d.

Also, as illustrated in FIGS. 2, 4, the opening and closing device H according to the present embodiment is held by a lid member 16 attached to a vertically movable shaft member 17. As illustrated in FIG. 4, upward lifting of the lid member 16 causes the opening and closing device H to be removed from the dialysate extraction device 10, and as illustrated in FIG. 2, downward pulling of the lid member 16 causes the opening and closing device H to be attached to the dialysate extraction device 10. It is to be noted that symbol R in FIGS. 2, 4 indicates a lock device that locks the lid member 16 with the opening and closing device H attached to the dialysate extraction device 10.

Here, in the dialysis device B of the blood purification apparatus according to the present embodiment, there are disposed a control means 19 that makes it possible to generate a pressure difference between the blood circuit side and the dialysate introduction line L1 side across the check valve 18; a monitor means 20 that makes it possible to monitor a change in a detection value of the pressure detection device ($\alpha$, $\beta$, $\gamma$) based on the pressure difference; and a determination means 21 that makes it possible to determine whether or not blocking of liquid by the check valve 18 is appropriate based on the change in the detection value of the pressure detection device (α, β, γ). It is to be noted that the pressure detection device (α) is configured to detect a pressure in the flow path of the dialysate introduction line L1, the pressure detection device (β) is configured to detect a pressure in the flow path of the dialysate discharge line L2, and the pressure detection device (γ) is configured to detect a pressure in the flow path of the blood circuit (particularly, the arterial blood circuit 2).

More specifically, the control means 19 makes it possible to generate a pressure difference between the blood circuit side and the dialysate introduction line L1 side across the check valve 18 by selectively performing opening and closing of any electromagnetic valves or clamp devices (V1 to V7, Va to Vc) and driving of any pump (such as the blood pump 4, a liquid level adjustment pump 23 (see FIG. 8), the duplex pump 7 as liquid delivery pump, the ultrafiltration pump 8 or the pressurizing pump 9) before treatment. The pressure difference is set such that the blood circuit side is higher in pressure than the dialysate introduction line side (the dialysate introduction line side is lower than the blood circuit side).

The monitor means 20 is electrically connected to the pressure detection device (α, β, γ), and can monitor change (increase, decrease, or retention of pressure) in one or plural of detection values of the pressure detection device (α, β, γ). The determination means 21 can determine whether the check function (function of blocking a flow of liquid from the blood circuit to the dialysate introduction line L1 of the check valve 18) is appropriate (flow of liquid can be sufficiently blocked) or inappropriate (flow of liquid cannot be sufficiently blocked) based on the change in the detection values of the pressure detection device (α, β, γ) monitored by the monitor means 20.

Hereinafter, an embodiment making it possible to determine before treatment whether or not the check valve 18 is appropriate by driving the blood pump 4 will be described based on the schematic diagram of FIG. 5 and the flow chart of FIG. 6. First, after priming is completed, a predetermined clamp device or electromagnetic valve is opened or closed by the control means 19 (S1), and as illustrated in FIG. 5, the clamp devices Va, Vb and the electromagnetic valves V1, V2, V4 to V7 are set to a closed state (the flow path is blocked) and the clamp device Vc and the electromagnetic valve V3 are set to an opened state (the flow path is opened). Thus, a closed circuit is formed in each of the dialysate introduction line L1 side (including the dialysate discharge line L2, the bypass lines L7, L8, the detour lines L3, L4, L5) and the blood circuit side (including the dialysate supply line La) across the dialysate extraction device 10, and the pressure detection devices (α, β) are connected in the closed circuit on the dialysate introduction line L1 side.

The blood pump 4 is then driven so as to reversely rotate (rotates in the direction opposite to the direction at the time of treatment) (S2), and priming liquid in the blood circuit is delivered to the leading end of the arterial blood circuit 2. Consequently, a pressure is applied to the priming liquid in the dialysate supply line La, and the check valve 18 disposed in the dialysate extraction device 10 is pressurized from the blood circuit side. Therefore, driving the blood pump 4 makes it possible to generate a pressure difference across the check valve 18 with the blood circuit side higher in pressure than the dialysate introduction line side.

Subsequently, change in the detection value of the pressure detection device α or the pressure detection device β is monitored by the monitor means 20, and presence or absence of a pressure increase (a pressure increase due to driving of the blood pump 4) is determined based on the change of the detection value (S3). When presence of a pressure increase is determined in S3, the check function (function of blocking a flow of liquid from the blood circuit to the dialysate introduction line L1) of the check valve 18 is determined to be inappropriate (flow of liquid cannot be sufficiently blocked) by the determination means 21, and when absence of a pressure increase is determined in S3, the check function is determined to be appropriate (flow of liquid can be sufficiently blocked). It is to be noted that when the check function is determined to be inappropriate, predetermined warning is given.

Furthermore, another embodiment making it possible to determine before treatment whether or not the check valve 18 is appropriate by driving the blood pump 4 will be described based on the schematic diagram of FIG. 5 and the flow chart of FIG. 7. First, after priming is completed, a predetermined clamp device or electromagnetic valve is opened or closed by the control means 19 (S1), and as illustrated in FIG. 5, the clamp devices Va, Vb and the electromagnetic valves V1, V2, V4 to V7 are set to a closed state (the flow path is blocked) and the clamp device Vc and the electromagnetic valve V3 are set to an opened state (the flow path is opened). Thus, a closed circuit is formed in each of the dialysate introduction line L1 side (including the dialysate discharge line L2, the bypass lines L7, L8, the detour lines L3, L4, L5) and the blood circuit side (including the dialysate supply line La) across the dialysate extraction device 10, and the pressure detection device α is connected in the closed circuit on the blood circuit side.

The blood pump 4 is then driven so as to reversely rotate (rotates in the direction opposite to the direction at the time of treatment) (S2), and priming liquid in the blood circuit is delivered to the leading end of the arterial blood circuit 2. Consequently, a pressure is applied to the priming liquid in the dialysate supply line La, and the check valve 18 disposed in the dialysate extraction device 10 is pressurized from the blood circuit side. Therefore, driving the blood pump 4 makes it possible to generate a pressure difference across the check valve 18 with the blood circuit side higher in pressure than the dialysate introduction line side.

Subsequently, change in the detection value of the pressure detection device (γ) is monitored by the monitor means 20, and presence or absence of a pressure increase (a pressure increase due to driving of the blood pump 4) is determined based on the change of the detection value, and when a pressure increase occurs, presence or absence of retention of the pressure for a predetermined time is determined (S3). When presence of a pressure increase and pressure retention is determined in S3, the check function of the check valve 18 is determined to be appropriate (flow of liquid can be sufficiently blocked) by the determination means 21. When absence of a pressure increase and pressure retention is determined in S3, the check function is determined to be inappropriate (flow of liquid cannot be sufficiently blocked). It is to be noted that when the check function is determined to be inappropriate, predetermined warning is given.

In this manner, since the blood pump 4 for flowing liquid in the blood circuit is attached to the arterial blood circuit 2 and the control means 19 can generate a pressure difference across the check valve 18 with the blood circuit side higher in pressure than the dialysate introduction line L1 side, it is possible to easily and accurately determine before treatment whether or not blocking of liquid by the check valve 18 is appropriate by utilizing the blood pump 4 which is necessary at the time of treatment.

Next, an embodiment making it possible to determine before treatment whether or not the check valve 18 is appropriate by driving the liquid level adjustment pump 23 will be described based on the schematic diagram of FIG. 8 and the flow chart of FIG. 9. The liquid level adjustment pump 23 is comprised of a peristaltic pump for adjusting a liquid level by introducing air into an air layer of the air trap chambers 5, 6 or discharging air from an air layer of the air trap chambers 5, 6 by opening or closing the electromagnetic valves V8, V9.

First, the leading end of the arterial blood circuit 2 and the leading end of the venous blood circuit 3 are connected and priming is completed, then a predetermined clamp device or electromagnetic valve is opened or closed by the control means 19 (S1), and as illustrated in FIG. 8, the electromagnetic valves V1, V2, V4 to V7, V9 are set to a closed state (the flow path is blocked) and the clamp devices Va, Vb, Vc and the electromagnetic valves V3, V8 are set to an opened state (the flow path is opened). Thus, a closed circuit is formed in each of the dialysate introduction line L1 side (including the dialysate discharge line L2, the bypass lines L7, L8, the detour lines L3, L4, L5) and the blood circuit side (including the dialysate supply line La) across the dialysate extraction device 10, and the pressure detection devices ($\alpha$, $\beta$) are connected in the closed circuit on the dialysate introduction line L1 side.

The liquid level adjustment pump 23 is then driven so as to rotate (rotate in a direction in which air is sent into the air trap chamber 6) (S2). Consequently, a pressure is applied to the priming liquid in the dialysate supply line La, and the check valve 18 disposed in the dialysate extraction device 10 is pressurized from the blood circuit side. Therefore, driving the liquid level adjustment pump 23 makes it possible to generate a pressure difference across the check valve 18 with the blood circuit side higher in pressure than the dialysate introduction line side.

Subsequently, change in the detection value of the pressure detection device $\alpha$ or the pressure detection device ($\beta$) is monitored by the monitor means 20, and presence or absence of a pressure increase (a pressure increase due to driving of the blood pump 4) is determined based on the change of the detection value (S3). When presence of a pressure increase is determined in S3, the check function (function of blocking a flow of liquid from the blood circuit to the dialysate introduction line L1) of the check valve 18 is determined to be inappropriate (flow of liquid cannot be sufficiently blocked) by the determination means 21, and when absence of a pressure increase is determined in S3, the check function is determined to be appropriate (flow of liquid can be sufficiently blocked). It is to be noted that when the check function is determined to be inappropriate, predetermined warning is given.

Furthermore, another embodiment making it possible to determine before treatment whether or not the check valve 18 is appropriate by driving the liquid level adjustment pump 23 will be described based on the schematic diagram of FIG. 8 and the flow chart of FIG. 10. First, the leading end of the arterial blood circuit 2 and the leading end of the venous blood circuit 3 are connected and priming is completed, then a predetermined clamp device or electromagnetic valve is opened or closed by the control means 19 (S1), and as illustrated in FIG. 8, the electromagnetic valves V1, V2, V4 to V7, V9 are set to a closed state (the flow path is blocked) and the clamp devices Va, Vb, Vc and the electromagnetic valves V3, V8 are set to an opened state (the flow path is opened). Thus, a closed circuit is formed in each of the dialysate introduction line L1 side (including the dialysate discharge line L2, the bypass lines L7, L8, the detour lines L3, L4, L5) and the blood circuit side (including the dialysate supply line La) across the dialysate extraction device 10, and the pressure detection device ($\gamma$) is connected in the closed circuit on the blood circuit side.

The liquid level adjustment pump 23 is then driven so as to rotate (rotate in a direction in which air is sent into the air trap chamber 6) (S2). Consequently, a pressure is applied to the priming liquid in the dialysate supply line La, and the check valve 18 disposed in the dialysate extraction device 10 is pressurized from the blood circuit side. Therefore, driving the liquid level adjustment pump 23 makes it possible to generate a pressure difference across the check valve 18 with the blood circuit side higher in pressure than the dialysate introduction line side.

Subsequently, change in the detection value of the pressure detection device ($\gamma$) is monitored by the monitor means 20, and presence or absence of a pressure increase (a pressure increase due to driving of the liquid level adjustment pump 23) is determined based on the change of the detection value, and when a pressure increase occurs, presence or absence of retention of the pressure for a predetermined time is determined (S3). When presence of a pressure increase and pressure retention is determined in S3, the check function of the check valve 18 is determined to be appropriate (flow of liquid can be sufficiently blocked) by the determination means 21. When absence of a pressure increase and pressure retention is determined in S3, the check function is determined to be inappropriate (flow of liquid cannot be sufficiently blocked). It is to be noted that when the check function is determined to be inappropriate, predetermined warning is given.

In this manner, since there are provided the air trap chamber 6 that is connected to the blood circuit, and that is for removing the air in the liquid flowing through the blood circuit; and the liquid level adjustment pump 23 for adjusting a liquid level by introducing air into an air layer of the air trap chamber 6 or discharging air from an air layer of the air trap chamber 6, and the control means 19 can generate a pressure difference across the check valve 18 with the blood circuit side higher in pressure than the dialysate introduction line L1 side by driving the liquid level adjustment pump 23, it is possible to easily and accurately determine before treatment whether or not blocking of liquid by the check valve 18 is appropriate by utilizing the liquid level adjustment pump 23 which is necessary before the treatment.

Next, an embodiment making it possible to determine before treatment whether or not the check valve 18 is appropriate by back-filtering will be described based on the schematic diagram of FIG. 11 and the flow chart of FIG. 12. The back-filtration is for filtering dialysate from the dialysate flow path (a flow path communicating with the dialysate introduction line L1 and the dialysate discharge line L2) to the blood flow path (a flow path communicating with the arterial blood circuit 2 and the venous blood circuit 3) via a filtration membrane (hollow fiber membrane) in the dialyzer 1.

First, the leading end of the arterial blood circuit 2 and the leading end of the venous blood circuit 3 are connected and priming is completed, then a predetermined clamp device or electromagnetic valve is opened or closed by the control means 19 (S1), and as illustrated in FIG. 11, the electromagnetic valves V1, V3 to V7 are set to a closed state (the flow path is blocked) and the clamp devices Va, Vb, Vc and the electromagnetic valve V2 are set to an opened state (the flow path is opened). Thus, a closed circuit is formed in each of the dialysate introduction line L1 side (including the dialysate discharge line L2, the bypass lines L7, L8, the detour lines L3, L4, L5) and the blood circuit side (including the dialysate supply line La) across the dialysate extraction device 10, and the pressure detection device α is connected in the closed circuit on the blood circuit side.

The ultrafiltration pump 8 is then driven so as to reversely rotate (rotates in the direction opposite to the direction at the time of treatment) (S2). Consequently, the dialysate of the dialysate discharge line L2 is back-filtered by the dialyzer 1, and thus a pressure is applied to the priming liquid in the dialysate supply line La, and the check valve 18 disposed in the dialysate extraction device 10 is pressurized from the blood circuit side. Therefore, the back-filtration makes it possible to generate a pressure difference across the check valve 18 with the blood circuit side higher in pressure than the dialysate introduction line side.

Subsequently, change in the detection value of the pressure detection device β or the pressure detection device (γ) is monitored by the monitor means 20, and presence or absence of a pressure increase (a pressure increase due to the back-filtration) is determined based on the change of the detection values (S3), and when a pressure increase occurs, presence or absence of retention of the pressure for a predetermined time is determined (S3). When presence of a pressure increase and pressure retention is determined in S3, the check function of the check valve 18 is determined to be appropriate (flow of liquid can be sufficiently blocked) by the determination means 21. When absence of a pressure increase and pressure retention is determined in S3, the check function is determined to be inappropriate (flow of liquid cannot be sufficiently blocked). It is to be noted that when the check function is determined to be inappropriate, predetermined warning is given.

Furthermore, another embodiment making it possible to determine before treatment whether or not the check valve 18 is appropriate by back-filtering will be described based on the schematic diagram of FIG. 11 and the flow chart of FIG. 13. First, the leading end of the arterial blood circuit 2 and the leading end of the venous blood circuit 3 are connected and priming is completed, then a predetermined clamp device or electromagnetic valve is opened or closed by the control means 19 (S1), and as illustrated in FIG. 11, the electromagnetic valves V1, V3 to V7 are set to a closed state (the flow path is blocked) and the clamp devices Va, Vb, Vc and the electromagnetic valve V2 are set to an opened state (the flow path is opened). Thus, a closed circuit is formed in each of the dialysate introduction line L1 side (including the dialysate discharge line L2, the bypass lines L7, L8, the detour lines L3, L4, L5) and the blood circuit side (including the dialysate supply line La) across the dialysate extraction device 10, and the pressure detection device α is connected in the closed circuit on the dialysate introduction line L1 side.

The ultrafiltration pump 8 is then driven so as to reversely rotate (rotates in the direction opposite to the direction at the time of treatment) (S2). Consequently, the dialysate of the dialysate discharge line L2 is back-filtered by the dialyzer 1, and thus a pressure is applied to the priming liquid in the dialysate supply line La, and the check valve 18 disposed in the dialysate extraction device 10 is pressurized from the blood circuit side. Therefore, the back-filtration makes it possible to generate a pressure difference across the check valve 18 with the blood circuit side higher in pressure than the dialysate introduction line side.

Subsequently, change in the detection value of the pressure detection device (α) is monitored by the monitor means 20, and presence or absence of a pressure increase (a pressure increase due to the back-filtration) is determined based on the change of the detection value (S3). When presence of a pressure increase is determined in S3, the check function (function of blocking a flow of liquid from the blood circuit to the dialysate introduction line L1) of the check valve 18 is determined to be inappropriate (flow of liquid cannot be sufficiently blocked) by the determination means 21, and when absence of a pressure increase is determined in S3, the check function is determined to be appropriate (flow of liquid can be sufficiently blocked). It is to be noted that when the check function is determined to be inappropriate, predetermined warning is given.

In this manner, the control means 19 can generate a pressure difference across the check valve 18 with the blood circuit side higher in pressure than the dialysate introduction line L1 side by back-filtering the dialysate of the dialysate introduction line L1 or the dialysate discharge line L2 in the dialyzer 1 (blood purification device) and introducing the dialysate into the blood circuit, and thus it is possible to easily and accurately determine before treatment whether or not blocking of liquid by the check valve 18 is appropriate by the back-filtering.

Next, an embodiment making it possible to determine before treatment whether or not the check valve 18 is appropriate by driving the ultrafiltration pump 8 will be described based on the schematic diagram of FIG. 14 and the flow chart of FIG. 15. First, after priming is completed, a predetermined clamp device or electromagnetic valve is opened or closed by the control means 19 (S1), and as illustrated in FIG. 14, the clamp devices Va, Vb and the electromagnetic valves V1, V2, V4 to V7 are set to a closed state (the flow path is blocked) and the clamp device Vc and the electromagnetic valve V3 are set to an opened state (the flow path is opened). Thus, a closed circuit is formed in each of the dialysate introduction line L1 side (including the dialysate discharge line L2, the bypass lines L7, L8, the detour lines L3, L4, L5) and the blood circuit side (including the dialysate supply line La) across the dialysate extraction device 10, and the pressure detection devices (α, β) are connected in the closed circuit on the dialysate introduction line L1 side.

The ultrafiltration pump 8 is then driven (to rotate in the same direction as the direction at the time of treatment) (S2), thereby generating a negative pressure on the dialysate introduction line L1 side with respect to the check valve 18. Therefore, driving the ultrafiltration pump 8 makes it possible to generate a pressure difference across the check valve 18 with the dialysate introduction line L1 side lower in pressure than the blood circuit side.

Subsequently, change in the detection value of the pressure detection device (α) or the pressure detection device (β) is monitored by the monitor means 20, and presence or absence of a pressure decrease (a pressure decrease due to driving of the ultrafiltration pump 8) is determined based on the change of the detection value, and when a pressure decrease occurs, presence or absence of retention of the pressure for a predetermined time is determined (S3). When presence of a pressure decrease and pressure retention is determined in S3, the check function of the check valve 18 is determined to be appropriate (flow of liquid can be sufficiently blocked) by the determination means 21. When absence of a pressure decrease and pressure retention is determined in S3, the check function is determined to be inappropriate (flow of liquid cannot be sufficiently blocked). It is to be noted that when the check function is determined to be inappropriate, predetermined warning is given.

Furthermore, another embodiment making it possible to determine before treatment whether or not the check valve 18 is appropriate by driving the ultrafiltration pump 8 will be described based on the schematic diagram of FIG. 14 and the flow chart of FIG. 16. First, after priming is completed, a predetermined clamp device or electromagnetic valve is opened or closed by the control means 19 (S1), and as illustrated in FIG. 14, the clamp devices Va, Vb and the electromagnetic valves V1, V2, V4 to V7 are set to a closed state (the flow path is blocked) and the clamp device Vc and the electromagnetic valve V3 are set to an opened state (the flow path is opened). Thus, a closed circuit is formed in each of the dialysate introduction line L1 side (including the dialysate discharge line L2, the bypass lines L7, L8, the detour lines L3, L4, L5) and the blood circuit side (including the dialysate supply line La) across the dialysate extraction device 10, and the pressure detection device α is connected in the closed circuit on the blood circuit side.

The ultrafiltration pump 8 is then driven (to rotate in the direction opposite to the direction at the time of treatment) (S2), thereby generating a negative pressure on the dialysate introduction line L1 side with respect to the check valve 18. Therefore, driving the ultrafiltration pump 8 makes it possible to generate a pressure difference across the check valve 18 with the dialysate introduction line L1 side lower in pressure than the blood circuit side.

Subsequently, change in the detection value of the pressure detection device (γ) is monitored by the monitor means 20, and presence or absence of a pressure decrease (a pressure decrease due to driving of the ultrafiltration pump 8) is determined based on the change of the detection value (S3). When presence of a pressure decrease is determined in S3, the check function (function of blocking a flow of liquid from the blood circuit to the dialysate introduction line L1) of the check valve 18 is determined to be inappropriate (flow of liquid cannot be sufficiently blocked) by the determination means 21, and when absence of a pressure decrease is determined in S3, the check function is determined to be appropriate (flow of liquid can be sufficiently blocked). It is to be noted that when the check function is determined to be inappropriate, predetermined warning is given.

In this manner, since the dialysate discharge line L2 is connected to the ultrafiltration pump 8 for performing ultrafiltration by removing water from blood flowing in the dialyzer 1 (blood purification device), and the control means 19 can generate a pressure difference across the check valve 18 with the dialysate introduction line L1 side lower in pressure than the blood circuit side by driving the ultrafiltration pump 8, it is possible to easily and accurately determine before treatment whether or not blocking of liquid by the check valve 18 is appropriate by utilizing the ultrafiltration pump 8 which is necessary at the time of treatment.

Next, an embodiment making it possible to determine before treatment whether or not the check valve 18 is appropriate by driving the duplex pump 7 (liquid delivery pump) will be described based on the schematic diagram of FIG. 17 and the flow chart of FIG. 18. It is to be noted that in the dialysate introduction line L1, a detour line L9 to make a detour around the duplex pump 7 is formed and an electromagnetic valve V10 is disposed in the detour line L9.

First, after priming is completed, a predetermined clamp device or electromagnetic valve is opened or closed by the control means 19 (S1), and as illustrated in FIG. 17, the clamp devices Va, Vb and the electromagnetic valves V1, V2, V4 to V7 are set to a closed state (the flow path is blocked) and the clamp device Vc and the electromagnetic valves V3, V10 are set to an opened state (the flow path is opened). Thus, a closed circuit is formed in each of the dialysate introduction line L1 side (including the dialysate discharge line L2, the bypass lines L7, L8, the detour lines L3, L4, L5) and the blood circuit side (including the dialysate supply line La) across the dialysate extraction device 10, and the pressure detection devices (α, β) are connected in the closed circuit on the dialysate introduction line L1 side.

The duplex pump 7 is then driven (S2), thereby generating a negative pressure on the dialysate introduction line L1 side with respect to the check valve 18. It is to be noted that when the duplex pump 7 is driven, the dialysate circulates in the detour line L9 and serves as a relief device, and thus the duplex pump 7 can be driven more smoothly. Therefore, driving the duplex pump 7 makes it possible to generate a pressure difference across the check valve 18 with the dialysate introduction line L1 side lower in pressure than the blood circuit side.

Subsequently, change in the detection value of the pressure detection device (α) or the pressure detection device (β) is monitored by the monitor means 20, and presence or absence of a pressure decrease (a pressure decrease due to driving of the ultrafiltration pump 8) is determined based on the change of the detection value, and when a pressure decrease occurs, presence or absence of retention of the pressure for a predetermined time is determined (S3). When presence of a pressure decrease and pressure retention is determined in S3, the check function of the check valve 18 is determined to be appropriate (flow of liquid can be sufficiently blocked) by the determination means 21. When absence of a pressure decrease and pressure retention is determined in S3, the check function is determined to be inappropriate (flow of liquid cannot be sufficiently blocked). It is to be noted that when the check function is determined to be inappropriate, predetermined warning is given.

Furthermore, another embodiment making it possible to determine before treatment whether or not the check valve 18 is appropriate by driving the duplex pump 7 will be described based on the schematic diagram of FIG. 17 and the flow chart of FIG. 19. First, after priming is completed, a predetermined clamp device or electromagnetic valve is opened or closed by the control means 19 (S1), and as illustrated in FIG. 17, the clamp devices Va, Vb and the electromagnetic valves V1, V2, V4 to V7 are set to a closed state (the flow path is blocked) and the clamp device Vc and the electromagnetic valves V3, V10 are set to an opened state (the flow path is opened). Thus, a closed circuit is formed in each of the dialysate introduction line L1 side (including the dialysate discharge line L2, the bypass lines L7, L8, the detour lines L3, L4, L5) and the blood circuit side (including the dialysate supply line La) across the dialysate extraction device 10, and the pressure detection device α is connected in the closed circuit on the blood circuit side.

The duplex pump 7 is driven (S2), thereby generating a negative pressure on the dialysate introduction line L1 side with respect to the check valve 18. It is to be noted that when the duplex pump 7 is driven, the dialysate circulates in the detour line L9 and serves as a relief device, and thus the duplex pump 7 can be driven more smoothly. Therefore, driving the duplex pump 7 makes it possible to generate a pressure difference across the check valve 18 with the dialysate introduction line L1 side lower in pressure than the blood circuit side.

Subsequently, change in the detection value of the pressure detection device (γ) is monitored by the monitor means 20, and presence or absence of a pressure decrease (a pressure decrease due to driving of the duplex pump 7) is determined based on the change of the detection value (S3). When presence of a pressure decrease is determined in S3, the check function (function of blocking a flow of liquid from the blood circuit to the dialysate introduction line L1) of the check valve 18 is determined to be inappropriate (flow of liquid cannot be sufficiently blocked) by the determination means 21, and when absence of a pressure decrease is determined in S3, the check function is determined to be appropriate (flow of liquid can be sufficiently blocked). It is to be noted that when the check function is determined to be inappropriate, predetermined warning is given.

In this manner, since there is provided the duplex pump 7 (liquid delivery pump) that allows dialysate to be introduced via the dialysate introduction line L1 and dialysate to be discharged via the dialysate discharge line L2 into and from the dialyzer 1 (blood purification device), and the control means 19 can generate a pressure difference across the check valve 18 with the dialysate introduction line L1 side lower in pressure than the blood circuit side by driving the duplex pump 7, it is possible to easily and accurately determine before treatment whether or not blocking of liquid by the check valve 18 is appropriate by utilizing the duplex pump 7 which is necessary at the time of treatment.

Next, an embodiment making it possible to determine before treatment whether or not the check valve 18 is appropriate by driving the pressurizing pump 9 will be described based on the schematic diagram of FIG. 20 and the flow chart of FIG. 21. The pressurizing pump 9 is connected to the dialysate discharge line L2 and allows the flow rate of the dialysate discharged by the duplex pump 7 (liquid delivery pump) to be adjusted in any manner. Also, the detour line L5 branches between the pressurizing pump 9 and the duplex pump 7 in the dialysate discharge line L2, and comprised of a flow path to make a detour around the duplex pump 7.

First, after priming is completed, a predetermined clamp device or electromagnetic valve is opened or closed by the control means 19 (S1), and as illustrated in FIG. 20, the clamp devices Va, Vb and the electromagnetic valves V1, V2, V4, V5, and V7 are set to a closed state (the flow path is blocked) and the clamp device Vc and the electromagnetic valves V3, V6 are set to an opened state (the flow path is opened). Thus, a closed circuit is formed in each of the dialysate introduction line L1 side (including the dialysate discharge line L2, the bypass lines L7, L8, the detour lines L3, L4, L5) and the blood circuit side (including the dialysate supply line La) across the dialysate extraction device 10, and the pressure detection devices (α, β) are connected in the closed circuit on the dialysate introduction line L1 side.

The pressurizing pump 9 is then driven (to rotate in the same direction as the direction at the time of treatment) (S2), thereby discharging the dialysate via the detour line L5 and generating a negative pressure on the dialysate introduction line L1 side with respect to the check valve 18. Therefore, driving the pressurizing pump 9 makes it possible to generate a pressure difference across the check valve 18 with the dialysate introduction line L1 side lower in pressure than the blood circuit side. It is to be noted that when a circulating pump is provided instead of the pressurizing pump 9, the circulating pump is driven, and the dialysate is made to flow in the detour line L5, and thus a pressure difference across the check valve 18 may be generated with the dialysate introduction line L1 side lower in pressure than the blood circuit side.

Subsequently, change in the detection value of the pressure detection device (α) or the pressure detection device (β) is monitored by the monitor means 20, and presence or absence of a pressure decrease (a pressure decrease due to driving of the pressurizing pump 9) is determined based on the change of the detection value, and when a pressure decrease occurs, presence or absence of retention of the pressure for a predetermined time is determined (S3). When presence of a pressure decrease and pressure retention is determined in S3, the check function of the check valve 18 is determined to be appropriate (flow of liquid can be sufficiently blocked) by the determination means 21. When absence of a pressure decrease and pressure retention is determined in S3, the check function is determined to be inappropriate (flow of liquid cannot be sufficiently blocked). It is to be noted that when the check function is determined to be inappropriate, predetermined warning is given.

Furthermore, another embodiment making it possible to determine before treatment whether or not the check valve 18 is appropriate by driving the pressurizing pump 9 will be described based on the schematic diagram of FIG. 20 and the flow chart of FIG. 22. First, after priming is completed, a predetermined clamp device or electromagnetic valve is opened or closed by the control means 19 (S1), and as illustrated in FIG. 20, the clamp devices Va, Vb and the electromagnetic valves V1, V2, V4, V5, and V7 are set to a closed state (the flow path is blocked) and the clamp device Vc and the electromagnetic valves V3, V6 are set to an opened state (the flow path is opened). Thus, a closed circuit is formed in each of the dialysate introduction line L1 side (including the dialysate discharge line L2, the bypass lines L7, L8, the detour lines L3, L4, L5) and the blood circuit side (including the dialysate supply line La) across the dialysate extraction device 10, and the pressure detection device (γ) is connected in the closed circuit on the blood circuit side.

The pressurizing pump 9 is then driven (to rotate in the direction opposite to the direction at the time of treatment) (S2), thereby discharging the dialysate via the detour line L5 and generating a negative pressure on the dialysate introduction line L1 side with respect to the check valve 18. Therefore, driving the pressurizing pump 9 makes it possible to generate a pressure difference across the check valve 18 with the dialysate introduction line L1 side lower in pressure than the blood circuit side.

Subsequently, change in the detection value of the pressure detection device (γ) is monitored by the monitor means 20, and presence or absence of a pressure decrease (a pressure decrease due to driving of the pressurizing pump 9) is determined based on the change of the detection value (S3). When presence of a pressure decrease is determined in S3, the check function (function of blocking a flow of liquid from the blood circuit to the dialysate introduction line L1) of the check valve 18 is determined to be inappropriate (flow of liquid cannot be sufficiently blocked) by the determination means 21, and when absence of a pressure decrease is determined in S3, the check function is determined to be appropriate (flow of liquid can be sufficiently blocked). It is to be noted that when the check function is determined to be inappropriate, predetermined warning is given.

In this manner, since there are provided the duplex pump 7 (liquid delivery pump) that allows dialysate to be introduced via the dialysate introduction line L1 and dialysate to be discharged via the dialysate discharge line L2 into and from the dialyzer 1 (blood purification device); the pressurizing pump 9 (or a circulating pump) connected to the dialysate discharge line L2; and the detour line L5 branching between the pressurizing pump 9 and the duplex pump 7 (liquid delivery pump) in the dialysate discharge line L2 and comprised of a flow path to make a detour around the duplex pump 7 (liquid delivery pump), and the control means 19 can generate a pressure difference across the check valve 18 with the dialysate introduction line L1 side lower in pressure than the blood circuit side by driving the pressurizing pump 9 (or a circulating pump) and causing the dialysate to flow through the detour line L5, it is possible to easily and accurately determine before treatment whether or not blocking of liquid by the check valve 18 is appropriate by utilizing the pressurizing pump 9 (or a circulating pump) which is necessary at the time of treatment.

According to a series of embodiments described above, since there are provided the control means 19 that makes it possible to generate a pressure difference between the blood circuit side and the dialysate introduction line L1 side across the check valve 18; the monitor means 20 that makes it possible to monitor a change in a detection value of the pressure detection device ($\alpha$ to $\gamma$) based on the pressure difference; and a determination means 21 that makes it possible to determine whether or not blocking of liquid by the check valve 18 is appropriate based on the change in the detection value of the pressure detection device ($\alpha$ to $\gamma$), it is possible to easily and accurately determine before treatment whether or not blocking of liquid by the check valve 18 is appropriate.

Although the embodiments have been described in the above, the present invention is not limited to these, and may be applicable, for instance, as illustrated in FIG. 23, to an embodiment in which a dialysate extraction device 10' not provided with a check valve is connected to the dialysate introduction line L1 and the check valve 24 is disposed in the dialysate supply line La. Even in this case, it is possible to easily and accurately determine before treatment whether or not blocking of liquid by the check valve 24 is appropriate because there are provided the control means 19 that makes it possible to generate a pressure difference between the blood circuit side and the dialysate introduction line L1 side across the check valve 24; the monitor means 20 that makes it possible to monitor a change in a detection value of the pressure detection device ($\alpha$ to $\gamma$) based on the pressure difference; and a determination means 21 that makes it possible to determine whether or not blocking of liquid by the check valve 24 is appropriate based on the change in the detection value of the pressure detection device ($\alpha$ to $\gamma$).

Furthermore, although the pressure detection device ($\gamma$) is connected to the arterial blood circuit 2 via the chamber 22 in the present embodiment, the chamber 22 and the pressure detection device ($\gamma$) may not be provided and the monitor means 20 may monitor the detection value of the pressure detection device ($\alpha$, $\beta$). It is to be noted that a blood purification apparatus to which the present embodiment is applied may have any configuration, and for instance, the dialysate may be introduced or discharged in the chamber instead of the duplex pump 7, or a blood purifier in another configuration instead of the dialyzer 1 may be provided. Alternatively, the clamp device Va to Vc may be an electromagnetic valve device in another configuration, that makes it possible to open and close a flow path.

The invention is applicable to a blood purification apparatus with a different external appearance or with another function added as long as the blood purification apparatus includes: a control means that makes it possible to generate a pressure difference across the check valve between the blood circuit side and the dialysate introduction line side; a monitor means that makes it possible to monitor a change in the detection value of the pressure detection device based on the pressure difference; and a determination means that makes it possible to determine whether or not blocking of liquid by the check valve is appropriate based on the change in the detection value of the pressure detection device.

REFERENCE SIGNS LIST

1 Dialyzer (blood purification device)
2 Arterial blood circuit
3 Venous blood circuit
4 Blood pump
5 Arterial air trap chamber
6 Venous air trap chamber
7 Duplex pump (liquid delivery pump)
8 Ultrafiltration pump
9 Pressurizing pump
10 Dialysate extraction device
11, 12 Filter
13 Chamber
14 Seal member
15 Cap member
16 Lid member
17 Shaft member
18, 24 Check valve
19 Control means
20 Monitor means
21 Determination means
22 Chamber
23 Liquid level adjustment pump
H Opening and closing device
$\alpha$, $\beta$, $\gamma$ Pressure detection device

The invention claimed is:
1. A blood purification apparatus comprising:
a blood circuit including an arterial blood circuit and a venous blood circuit for extracorporeally circulating blood of a patient;
a blood purification device that is connected between the arterial blood circuit and the venous blood circuit, and that purifies the blood which flows through the blood circuit;
a dialysate introduction line that introduces dialysate into the blood purification device and a dialysate discharge line that discharges dialysate from the blood purification device;
a pressure detection device that is configured to detect a pressure in the dialysate introduction line or the dialysate discharge line, or a pressure in the blood circuit;
a dialysate extraction device which is connected to the dialysate introduction line, and in which an extraction port through which the flowing dialysate is extractable is formed;
a dialysate supply line with one end connected to the extraction port of the dialysate extraction device and the other end connected to the blood circuit, the dialysate supply line is configured to supply the dialysate of the dialysate introduction line to the blood circuit; and
a check valve that is connected to the dialysate extraction device or the dialysate supply line, that allows a flow of liquid from the dialysate introduction line to the blood circuit and blocks a flow of liquid from the blood circuit to the dialysate introduction line, wherein the blood purification apparatus includes:
a controller that generates a pressure difference across the check valve between a side of the blood circuit and a side of the dialysate introduction line;
a monitor that monitors a change in a detection value of the pressure detection device based on the pressure difference, and whether or not blocking of liquid by the check valve is appropriate is based on the change in the detection value of the pressure detection device being monitored.

2. The blood purification apparatus according to claim 1, wherein a blood pump for flowing liquid in the blood circuit is attached to the arterial blood circuit, and the controller drives the blood pump, thereby configured to generate a pressure difference across the check valve with the blood circuit side higher in pressure than the dialysate introduction line side.

3. The blood purification apparatus according to claim 1, further comprising:
an air trap chamber that is connected to the blood circuit, and that is for removing air in the liquid flowing in the blood circuit; and
a liquid level adjustment pump for adjusting a liquid level by introducing air into an air layer of the air trap chamber or discharging air from an air layer of the air trap chamber,
wherein the controller drives the liquid level adjustment pump, thereby configured to generate a pressure difference across the check valve with the blood circuit side higher in pressure than the dialysate introduction line side.

4. The blood purification apparatus according to claim 1, wherein the controller back-filters the dialysate of the dialysate introduction line or the dialysate discharge line by the blood purification device, and introduces the dialysate into the blood circuit, thereby configured to generate a pressure difference across the check valve with the blood circuit side higher in pressure than the dialysate introduction line side.

5. The blood purification apparatus according to claim 1, wherein the dialysate discharge line is connected to an ultrafiltration pump for performing ultrafiltration by removing water from the blood flowing in the blood purification device, and the controller drives the ultrafiltration pump, thereby configured to generate a pressure difference across the check valve with the dialysate introduction line side lower in pressure than the blood circuit side.

6. The blood purification apparatus according to claim 1, further comprising a liquid delivery pump that is configured to introduce the dialysate into the dialysate introduction line and to discharge the dialysate from the dialysate discharge line into and from the blood purification device, wherein the controller drives the liquid delivery pump, thereby configured to generate a pressure difference across the check valve with the dialysate introduction line side lower in pressure than the blood circuit side.

7. The blood purification apparatus according to claim 1, further comprising:
a liquid delivery pump that is configured to introduce the dialysate into the dialysate introduction line and to discharge the dialysate from the dialysate discharge line into and from the blood purification device;
a pressurizing pump or a circulating pump connected to the dialysate discharge line; and
a detour line comprised of a flow path which branches between the pressurizing pump and the liquid delivery pump in the dialysate discharge line, and which makes a detour around the liquid delivery pump,
wherein the controller drives the pressurizing pump or the circulating pump and causes the dialysate to flow through the detour line, thereby configured to generate a pressure difference across the check valve with the dialysate introduction line side lower in pressure than the blood circuit side.

8. A blood purification apparatus comprising:
a blood circuit including an arterial blood circuit and a venous blood circuit for extracorporeally circulating blood of a patient;
a blood purification device that is connected between the arterial blood circuit and the venous blood circuit, and that purifies the blood which flows through the blood circuit;
a dialysate introduction line that introduces dialysate into the blood purification device and a dialysate discharge line that discharges dialysate from the blood purification device;
a dialysate extraction device which is connected to the dialysate introduction line, and in which an extraction port through which the flowing dialysate is extractable is formed;
a dialysate supply line with one end connected to the extraction port of the dialysate extraction device and the other end connected to the blood circuit, the dialysate supply line is configured to supply the dialysate of the dialysate introduction line to the blood circuit;
a check valve that is connected to the dialysate extraction device or the dialysate supply line, that allows a flow of liquid from the dialysate introduction line to the blood circuit and blocks a flow of liquid from the blood circuit to the dialysate introduction line;
a pressure device that detects a pressure in the dialysate introduction line, the dialysate discharge line, or a pressure in the blood circuit, wherein a value of the pressure is monitored based on a pressure difference and whether or not blocking of liquid by a check valve is appropriate is based on the change in value of the pressure being monitored; and
a controller that generates a pressure difference across the check valve between a side of the blood circuit and a side of the dialysate introduction line by selectively performing opening and closing of one or more electromagnetic valves or clamp devices located within the blood circuit, driving one or more pumps within the blood circuit, or both.

9. The blood purification apparatus according to claim 1, wherein a blood pump for flowing liquid in the blood circuit is attached to the arterial blood circuit, and the controller drives the blood pump, thereby configured to generate a pressure difference across the check valve with the blood circuit side higher in pressure than the dialysate introduction line side.

10. The blood purification apparatus according to claim 1, further comprising:
an air trap chamber that is connected to the blood circuit, and that is for removing air in the liquid flowing in the blood circuit; and
a liquid level adjustment pump for adjusting a liquid level by introducing air into an air layer of the air trap chamber or discharging air from an air layer of the air trap chamber,
wherein the controller drives the liquid level adjustment pump, thereby configured to generate a pressure difference across the check valve with the blood circuit side higher in pressure than the dialysate introduction line side.

11. The blood purification apparatus according to claim 1, wherein the controller back-filters the dialysate of the dialysate introduction line or the dialysate discharge line by the blood purification device, and introduces the dialysate into the blood circuit, thereby configured to generate a pressure difference across the check valve with the blood circuit side higher in pressure than the dialysate introduction line side.

12. The blood purification apparatus according to claim 1, wherein the dialysate discharge line is connected to an ultrafiltration pump for performing ultrafiltration by removing water from the blood flowing in the blood purification device, and the controller drives the ultrafiltration pump, thereby configured to generate a pressure difference across the check valve with the dialysate introduction line side lower in pressure than the blood circuit side.

13. The blood purification apparatus according to claim 1, further comprising a liquid delivery pump that is configured to introduce the dialysate into the dialysate introduction line and to discharge the dialysate from the dialysate discharge line into and from the blood purification device, wherein the controller drives the liquid delivery pump, thereby configured to generate a pressure difference across the check valve with the dialysate introduction line side lower in pressure than the blood circuit side.

14. The blood purification apparatus according to claim 1, further comprising:
 a liquid delivery pump that is configured to introduce the dialysate into the dialysate introduction line and to discharge the dialysate from the dialysate discharge line into and from the blood purification device;
 a pressurizing pump or a circulating pump connected to the dialysate discharge line; and
 a detour line comprised of a flow path which branches between the pressurizing pump and the liquid delivery pump in the dialysate discharge line, and which makes a detour around the liquid delivery pump,
 wherein the controller drives the pressurizing pump or the circulating pump and causes the dialysate to flow through the detour line, thereby configured to generate a pressure difference across the check valve with the dialysate introduction line side lower in pressure than the blood circuit side.

* * * * *